United States Patent
Hoskuldsson et al.

(10) Patent No.: US 10,869,619 B2
(45) Date of Patent: Dec. 22, 2020

(54) METHOD, APPARATUS, AND SYSTEM FOR MEASURING RESPIRATORY EFFORT OF A SUBJECT

(71) Applicant: NOX MEDICAL, Reykjavik (IS)

(72) Inventors: Sveinbjorn Hoskuldsson, Reykjavik (IS); Jon Skirnir Agustsson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 199 days.

(21) Appl. No.: 15/680,910

(22) Filed: Aug. 18, 2017

(65) Prior Publication Data

US 2018/0049678 A1 Feb. 22, 2018

Related U.S. Application Data

(60) Provisional application No. 62/377,258, filed on Aug. 19, 2016.

(51) Int. Cl.
*A61B 5/113* (2006.01)
*A61B 5/087* (2006.01)
(Continued)

(52) U.S. Cl.
CPC .......... *A61B 5/1135* (2013.01); *A61B 5/0806* (2013.01); *A61B 5/087* (2013.01);
(Continued)

(58) Field of Classification Search
CPC .............................. A61B 5/087; A61B 5/6831
See application file for complete search history.

(56) References Cited

U.S. PATENT DOCUMENTS

| 937,130 A | 10/1909 | Williams |
|---|---|---|
| 1,115,459 A | 10/1914 | Abizaid |

(Continued)

FOREIGN PATENT DOCUMENTS

| DE | 19941500 A1 | 3/2001 |
|---|---|---|
| EP | 2324760 A2 | 5/2011 |

(Continued)

OTHER PUBLICATIONS

De Groote et al., "Mathematical Assessment of Qualitative Diagnostic Calibration for Respiratory Inductive Plethysmorgraphy," Journal of Applied Physiology, vol. 90, 2001, pp. 1025-1030.
(Continued)

*Primary Examiner* — Gary Jackson
*Assistant Examiner* — Zahed Kabir
(74) *Attorney, Agent, or Firm* — Workman Nydegger

(57) ABSTRACT

A method, apparatus, and system for measuring respiratory effort of a subject are provided. According to the method, a thoracic effort signal (T) is obtained, the thoracic effort signal (T) being an indicator of a thoracic component of the respiratory effort. An abdomen effort signal (A), the abdomen effort signal (A) being an indicator of an abdominal component of the respiratory effort. A respiratory flow (F) is obtained. The respiratory effort is determined by adjusting the components of a model of the respiratory system based on the thoracic effort signal (T), the abdomen effort signal (A), or the respiratory flow (F) or any combination of the thoracic effort signal (T), the abdomen effort signal (A), and the respiratory flow (F).

23 Claims, 12 Drawing Sheets

(51) Int. Cl.
*A61B 5/00* (2006.01)
*A61B 5/08* (2006.01)

(52) U.S. Cl.
CPC .......... *A61B 5/6823* (2013.01); *A61B 5/6831* (2013.01); *A61B 5/7278* (2013.01)

(56) References Cited

U.S. PATENT DOCUMENTS

| | | |
|---|---|---|
| 1,193,050 A | 8/1916 | Orewiler |
| 2,305,277 A | 12/1942 | Sloane et al. |
| 2,649,573 A | 8/1953 | Goldberg et al. |
| 2,667,159 A | 1/1954 | Goldberg et al. |
| 3,092,759 A | 6/1963 | Sommer |
| 3,347,223 A | 10/1967 | Pacela |
| 3,500,823 A | 3/1970 | Richardson et al. |
| 3,560,845 A | 2/1971 | Goldber et al. |
| 3,685,105 A | 8/1972 | Carlile et al. |
| 4,308,872 A | 1/1982 | Watson et al. |
| 4,373,534 A | 2/1983 | Watson |
| 4,430,777 A | 2/1984 | Takeda |
| 4,671,591 A | 6/1987 | Archer |
| 4,777,962 A | 10/1988 | Watson et al. |
| 4,807,640 A | 2/1989 | Watson et al. |
| 4,815,473 A | 3/1989 | Watson et al. |
| 4,817,625 A | 4/1989 | Miles |
| 4,832,608 A | 5/1989 | Kroll |
| 4,834,109 A | 5/1989 | Watson |
| 4,842,557 A | 6/1989 | Muz |
| 5,301,678 A | 4/1994 | Watson et al. |
| 5,326,272 A | 7/1994 | Harhen et al. |
| 5,331,968 A | 7/1994 | Williams et al. |
| 5,348,008 A | 9/1994 | Bornn et al. |
| 5,353,793 A | 10/1994 | Bornn |
| 5,543,012 A | 8/1996 | Watson et al. |
| 6,148,486 A | 11/2000 | Uehara et al. |
| 6,327,486 B1 | 12/2001 | Nissila et al. |
| 6,341,504 B1 | 1/2002 | Istook |
| 6,413,225 B1 | 6/2002 | Sackner et al. |
| 6,461,307 B1 | 10/2002 | Kristbjarnarson et al. |
| 6,807,438 B1 | 10/2004 | Brun Del Re et al. |
| 6,993,378 B2 | 1/2006 | Wiederhold et al. |
| 7,171,265 B2 | 1/2007 | Hoium et al. |
| 7,267,652 B2 | 9/2007 | Coyle et al. |
| 7,593,767 B1 | 9/2009 | Modarres |
| 7,604,603 B2 | 10/2009 | Sackner et al. |
| 7,670,295 B2 | 3/2010 | Sackner et al. |
| 7,727,161 B2 | 6/2010 | Coyle et al. |
| 7,762,953 B2 | 7/2010 | Derchak et al. |
| 7,819,710 B2 | 10/2010 | McIntire et al. |
| 7,878,979 B2 | 2/2011 | Derchak |
| 7,914,350 B1 | 3/2011 | Bozich et al. |
| 3,025,539 A1 | 9/2011 | Hermannsson |
| 8,025,539 B2 | 9/2011 | Hermannsson |
| 8,033,996 B2 | 10/2011 | Behar |
| 8,034,001 B2 | 10/2011 | Gal |
| 8,052,612 B2 | 11/2011 | Tang et al. |
| 8,137,270 B2 | 3/2012 | Keenan et al. |
| 8,165,654 B2 | 4/2012 | Tang et al. |
| 8,177,724 B2 | 5/2012 | Derchak et al. |
| 8,193,821 B2 | 6/2012 | Mueller et al. |
| 8,251,736 B2 | 8/2012 | McIntire et al. |
| 8,475,387 B2 | 7/2013 | Derchak et al. |
| 8,579,794 B2 | 11/2013 | Henke |
| 8,628,480 B2 | 1/2014 | Derchak |
| 8,679,012 B1 | 3/2014 | Kayyali |
| 8,762,733 B2 | 6/2014 | Derchak et al. |
| 8,777,868 B2 | 7/2014 | Gal |
| 8,790,255 B2 | 7/2014 | Behar |
| 8,790,272 B2 | 7/2014 | Sackner et al. |
| 9,059,532 B2 | 6/2015 | Hermannsson |
| 9,192,316 B2 | 11/2015 | Hoskuldsson et al. |
| 10,011,054 B1 | 7/2018 | Lee |
| 2002/0032386 A1 | 3/2002 | Sackner et al. |
| 2002/0032388 A1 | 3/2002 | Kristbjarnarson et al. |
| 2002/0120207 A1 | 8/2002 | Hoffman |
| 2003/0100843 A1* | 5/2003 | Hoffman .............. A61B 5/0809 600/538 |
| 2003/0135127 A1 | 7/2003 | Sackner et al. |
| 2005/0054941 A1 | 3/2005 | Ting et al. |
| 2005/0119586 A1 | 6/2005 | Coyle et al. |
| 2006/0122528 A1 | 6/2006 | Gal |
| 2006/0258948 A1 | 11/2006 | Linville |
| 2006/0282001 A1 | 12/2006 | Noel et al. |
| 2007/0167089 A1 | 7/2007 | Gobron et al. |
| 2008/0072912 A1* | 3/2008 | Scott ................. A61M 16/0468 128/207.14 |
| 2009/0159082 A1* | 6/2009 | Eger .................... A61B 5/0488 128/204.23 |
| 2009/0259135 A1 | 10/2009 | Stasz |
| 2010/0060300 A1 | 3/2010 | Muller et al. |
| 2010/0075527 A1 | 3/2010 | McIntire et al. |
| 2010/0075549 A1 | 3/2010 | McIntire et al. |
| 2010/0297868 A1 | 11/2010 | Hermannsson |
| 2011/0151728 A1 | 6/2011 | Astola |
| 2011/0192400 A9* | 8/2011 | Burton .................. A61M 16/10 128/204.23 |
| 2011/0248729 A2 | 10/2011 | Mueler et al. |
| 2012/0101357 A1 | 4/2012 | Hoskuldsson et al. |
| 2014/0323847 A1 | 10/2014 | Mccool |
| 2015/0038867 A1* | 2/2015 | Armitstead .......... A61B 5/0826 600/538 |
| 2015/0126879 A1* | 5/2015 | Hoskuldsson ....... A61B 5/0806 600/484 |
| 2015/0280348 A1 | 10/2015 | Hermannsson |
| 2016/0067433 A1* | 3/2016 | Martin ................. A61B 5/0826 128/204.23 |
| 2016/0073921 A1 | 3/2016 | Hoskuldsson et al. |
| 2016/0135715 A1 | 5/2016 | Seppä et al. |
| 2017/0110823 A1 | 4/2017 | Hermannsson et al. |
| 2017/0143206 A1 | 5/2017 | Kotz et al. |

FOREIGN PATENT DOCUMENTS

| | | |
|---|---|---|
| EP | 2324761 A2 | 5/2011 |
| EP | 2417905 A1 | 2/2012 |
| EP | 2484276 A2 | 8/2012 |
| EP | 2484277 A2 | 8/2012 |
| EP | 2484278 A3 | 8/2012 |
| EP | 2508123 A1 | 10/2012 |
| EP | 2508124 A2 | 10/2012 |
| EP | 2584962 A2 | 5/2013 |
| EP | 2589335 A2 | 5/2013 |
| WO | 0202013 A1 | 1/2002 |
| WO | 02080761 A2 | 10/2002 |
| WO | 2006024024 A2 | 3/2006 |
| WO | 20006066566 A2 | 6/2006 |
| WO | 2008102140 A1 | 8/2008 |
| WO | D071077-002 | 10/2008 |
| WO | 20080133394 A1 | 11/2008 |
| WO | 2011029136 A1 | 3/2011 |
| WO | 2018033889 A1 | 2/2018 |

OTHER PUBLICATIONS

Konno et al., "Measurement of the Separate Volume Changes of Rib Cage and Abdomen During Breathing," Journal of Applied Physiology, vol. 22, No. 3, 1967, pp. 407-422.

Sackner et al., "Calibration of Respiratory Inductive Plethysmograph During Natural Breathing," Journal of Applied Physiology, vol. 66, No. 1, 1989, pp. 410-420.

International Search Report from PCT Application No. PCT/IB2017/053128, dated Aug. 9, 2017.

Minutes of OP and Interlocutory Decision from Application No. 11 758 266.8, Nov. 6, 2017.

Notification of Minutes and Amendments at OP from Application No. 11 758 266.8, Nov. 6, 2017.

OP Decision and Reasoning from Application No. 11 758 266.8, Nov. 6, 2017.

Opposition against EP Application No. 11758266.8, Dec. 16, 2015.

Letter containing Test Results from European Patent No. 2584962, Feb. 23, 2017.

(56) References Cited

OTHER PUBLICATIONS

Escobar et al., "Nu-Way Snaps and Snap Leads: an Important Connection in the History of Behavior Analysis," Behav Analyst, 2014, vol. 37, pp. 95-107.
Declaration of Mr. Ami Vilhjalmsson, Apr. 11, 2017, 3 Pages.
Declaration of Mr. Hilmarsson, Apr. 6, 2017, 1 Page.
Declaration of Ms. Erna Sif Amardottir, 1 Page, Apr. 21, 2017.
Agustsson et al., "White Paper RIP Signal Assessment," Apr. 21, 2017, 21 Pages.
Statement of Mr. Sveinbjorn Hoskuldsson, Apr. 24, 2017, 2 Pages.
Statement from Mr. Andres Einar Hilmarsson, Apr. 24, 2017, 1 Page.
Declaration of Ms. Erla S. Amadottir, Apr. 25, 2017. 5 Pages.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
International Search Report from PCT Application No. PCT/IS2011/050010, dated Feb. 29, 2012.
International Search Report from PCT Application No. PCT/IB2014/002760, dated Mar. 27, 2015.
International Preliminary Report on Patentability from PCT Application No. PCT/IB2014/002760, dated May 10, 2016.
"Opinion Regarding European Patent, 2584962", Kilbun & Strode, dated Mar. 11, 2015, 14 Pages.
Notice of Appeal, Western High Court, Cephalon A/S, VS, Nox Medical Ehf, Mar. 9, 2015, 10 Pages.
"Defendant's Preliminary Invalidity and Unenforceability Contentions," Nox Medical EHF v. Natus Neurology Inc., Defendants, Civil Action No. 1:15-cv-00709-RGA, in the United States District Court for the District of Delaware, Apr. 15, 2016, 117 Pages.
"Defendant's First Supplemental Invalidity and Unenforceability Contentions," Nox Medical EHF v. Natus Neurology Inc., Defendants, Civil Action No. 1:15-cv-00709-RGA, in the United States District Court for the District of Delaware, Dec. 1, 2016, 3 Pages.
"Defendant's Second Supplemental Invalidity and Unenforceability Contentions," Nox Medical EHF v. Natus Neurology Inc., Defendants, Civil Action No. 1:15-cv-00709-RGA, in the United States District Court for the District of Delaware, 2009, 59 Pages.
"Defendant's Third Supplemental Invalidity and Unenforceability Contentions," Nox Medical EHF v. Natus Neurology Inc., Civil Action No. 1:15-cv-00709-RGA, in the United States District Court for the District of Delaware, Feb. 17, 2017, 4 Pages.
Patent Owner's Preliminary Response to U.S. Pat. No. 9,059,532, Dec. 27, 2016. 86 Pages.
Response to Opposition for European Patent No. 2584962, Nov. 23, 2015, 154 Pages.
"Disposable and Accessories Catalog for Respiratory Diagnostics", CareFusion, Natus Medical Inc., 2009, 138 Pages.
Petition for Inter Partes Review of U.S. Pat. No. 9,059,532, Sep. 15, 2016.
International Search Report from PCT Application No. PCT/IS2010/000007, dated Oct. 1, 2010.
Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.
Stromberg, N.O.T., "Error analysis of a natural breathing calibration method for respiratory inductive plethysmography", Medical & Biological Engineering & Computing 2001, vol. 39, No. 3, May 1, 2001, pp. 310-314.
Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.

Attachment A, to Natus' Third Supplemental Invalidity and Unenforceability Contentions, U.S. Pat. No. 9,059,532, Nox Medical Ehf. v. Natus Neurology, Inc., Civil Action No. 15-cv-00709-RGA (D. Del), 63 Pages.
Sackner et al., "Calibration of Respiratory Inductive Plethysmograph During Natural Breathing", The American Physiological Society, vol. 66, 1989, pp. 410-420.
Konno et al., "Static Volume-Pressure Characteristics of the Rib Cage and Abdomen", Journal of Applied Physiology, vol. 24, No. 4, Apr. 1968, pp. 544-548.
Agha et al., "Facial Phenotype in Obstructive Sleep Apnea-Hypopnea Syndrome: A Systematic Review and Meta-Analysis," Journal of Sleep Research, vol. 26, 2017, pp. 122-131.
Agrawal et al., "Sound Frequency Analysis and the Site of Snoring in Natural and Induced Sleep," Clinical Otolaryngology, vol. 27, 2002, pp. 162-166.
Akoumianaki et al., "The Application of Esophageal Pressure Measurement in Patients with Respiratory Failure," American Journal of Respiratory and Critical Care Medicine, vol. 189, No. 5, Mar. 1, 2014, pp. 520-531.
Arnardottir et al., "Snoring—Validation of Different Objective Measurements," European Respiratory Society Annual Congress 2013, 1 Page.
Arnardottir et al., "How to Measure Snoring? A Comparison of the Microphone, Cannula and Piezoelectric Sensor," Journal of Sleep Research, vol. 25, 2016, pp. 158-168.
Arnardottir et al., "Obstructive Sleep Apnoea in the General Population: Highly Prevalent but Minimal Symptoms," European Respiratory Journal, vol. 47, 2016, pp. 194-202.
Ayappa et al., "Non-Invasive Detection of Respiratory Effort-Related Arousals (RERAs) by a Nasal Cannula/Pressure Transducer System," Sleep, vol. 23, No. 6, 2000, pp. 763-771.
Berry et al., "Use of Chest Wall Electromyography to Detect Respiratory Effort During Polysomnography," Journal of Clinical Sleep Medicine, vol. 12, No. 9, 2016, pp. 1239-1244.
Berry et al., "AASM Scoring Manual Updates for 2017 (Version 2.4)," Journal of Clinical Sleep Medicine, vol. 13, No. 5, 2017, pp. 665-666.
Bloch et al., "Breathing Pattern During Sleep Disruptive Snoring," European Respiratory Journal, vol. 10, 1997, pp. 576-586.
Capistrano et al., "Facial Morphology and Obstructive Sleep Apnea," Dental Press Journal of Orthodontics, vol. 20, No. 6, Nov. 2015, pp. 60-67.
Eckert et al., "Pathophysiology of Adult Obstructive Sleep Apnea," Proceedings of the American Thoracic Society, vol. 5, 2008, pp. 144-153.
Faber et al., "Available Techniques for Objective Assessment of Upper Airway Narrowing in Snoring and Sleep Apnea," Sleep and Breathing, vol. 7, No. 2, 2003, pp. 77-86.
Ghafarian et al., "A Review on Human Respiratory Modeling," Tanaffos, vol. 15, No. 2, 2016, pp. 61-69.
Guilleminault et al., "Variability of Respiratory Effort in Relation to Sleep Stages in Normal Controls and Upper Airway Resistance Syndrome Patients," Sleep Medicine, vol. 2, 2001, pp. 397-406.
Harris et al., "GPCR Signalling in Hypertension: Role of GRKs," Clinical Science, vol. 115, 2008, pp. 79-89.
Heinzer et al., "Prevalence of Sleep-Disordered Breathing in the General Population: the HypnoLaus Study," Lancet Respiratory Medicine, vol. 3, No. 4, Apr. 2015, pp. 310-318.
Huo et al., "Endoscopic Upper Airway Evaluation in Obstructive Sleep Apnea: Mueller's Maneuver Versus Simulation of Snoring," Sleep Breath, vol. 19, 2015, pp. 661-667.
Konno et al., "Measurement of the Separate Volume," Journal of Applied Physiology, vol. 22, No. 3, 1967, pp. 407-422.
Kushida et al., "Technical Protocol for the use of Esophageal Manometry in the Diagnosis of Sleep-Related Breathing Disorders," Sleep Medicine, vol. 3, 2002, pp. 163-173.
Lee et al., "Energy Types of Snoring Sounds in Patients with Obstructive Sleep Apnea Syndrome: A Preliminary Observation," PLoS One, vol. 7, No. 12, Dec. 2012, 11 Pages.
Luo et al., "Diaphragm Electromyography Using an Oesophageal Catheter: Current Concepts," Clinical Science, vol. 115, 2008, pp. 233-244.

(56) References Cited

OTHER PUBLICATIONS

Masa et al., "Apnoeic and Obstructive Nonapnoeic Sleep Respiratory Events," European Respiratory Journal, vol. 34, 2009, pp. 156-161.

Otis et al., "Mechanical Factors in Distribution of Pulmonary Ventilation," Journal of Applied Physiology, vol. 8, No. 4, Jan. 1956, pp. 427-443.

Peppard et al., "Increased Prevalence of Sleep-Disordered Breathing in Adults," American Journal of Epidemiology, vol. 177, No. 9, Apr. 14, 2013, pp. 1006-1014.

Spinowitz et al., "Patterns of Upper Airway Obstruction on Drug-Induced Sleep Endoscopy in Patients with Sleep-Disordered Breathing with AHI < 5," American Academy of Otolaryngology—Head and Neck Surgery, 2017, 6 Pages.

Terrill et al., "Quantifying the Ventilatory Control Contribution to Sleep Apnoea Using Polysomnography," European Respiratory Journal, vol. 45, 2015, pp. 408-418.

Vandenbussche et al., "Assessment of Respiratory Effort During Sleep: Esophageal Pressure Versus Noninvasive Monitoring Techniques," Sleep Medicine Reviews, vol. 24, 2015, pp. 28-36.

Wellman et al., "A Method for Measuring and Modeling the Physiological Traits Causing Obstructive Sleep Apnea," Journal of Applied Physiology, vol. 110, 2011, pp. 1627-1637.

Wilson, "Compartmental Models of the Chest Wall and the Origin of Hoover's Sign," Respiratory Physiology & Neurobiology, vol. 210, 2015, pp. 23-29.

Duarte, "Detect Peaks in Data Based on Their Amplitude and Other Features.," retrieved from https://github.com/demotu/BMC/blob/master/functions/detect_peaks.py on Jun. 1, 2018, Oct. 3, 2014, 3 Pages.

Jones et al., "SciPy: Open Source Scientific Tools for Python," requested from http://www.scipy.org on Jun. 4, 2018, 2001, 3 Pages.

Orphanidou et al., "Signal-Quality Indices for the Electrocardiogram and Photoplethysmogram: Derivation and Applications to Wireless Monitoring," IEEE Journal of Biomedical and Health Informatics, vol. 19, No. 3, May 2015, pp. 832-838.

Roebuck et al., "A Review of Signals Used in Sleep Analysis," Physiological Measurement, vol. 35, 2014, pp. R1-R57.

International Search Report from PCT Application No. PCT/IB2018/053993, dated Aug. 24, 2018.

Lester et al., ""Are You With Me?"—Using Accelerometers to Determine if Two Devices are Carried by the Same Person," Pervasive, 2004, pp. 33-50.

Nino et al., "Robust Spectral Analysis of Thoraco-Abdominal Motion and Oxymetry in Obstructive Sleep Apnea," 35th Annual International Conference of the IEEE EMBS, Jul. 3, 2013, pp. 2906-2910.

Augousti et al., "Comparative Analysis of the Isovolume Calibration Method for Non-Invasive Respiratory Monitoring Techniques Based on Area Transduction Versus Circumference Transduction Using the Connected Cylinders Model," Physiological Measurement, vol. 32, 2011, pp. 1265-1274.

International Search Report and Written Opinion from PCT Application No. PCT/IB2018/056892, dated Dec. 13, 2018.

\* cited by examiner

METHOD, APPARATUS, AND SYSTEM FOR MEASURING RESPIRATORY EFFORT OF A SUBJECT

CROSS-REFERENCE TO RELATED APPLICATIONS

This application claims the benefit of U.S. Provisional Application No. 62/377,258, filed on Aug. 19, 2016, the entire contents of which are herein incorporated by reference.

FIELD OF THE DISCLOSURE

The present disclosure relates to a method, apparatus, and system for measuring respiratory effort of a subject, and to a method, apparatus, and system for calculating a calibration factor for calibrating signals representative of the respiratory effort of a subject.

BACKGROUND

Respiratory effort is a term used for indirect measures of the power needed to drive the respiratory airflow. The gold standard measure that has been used is an esophageal pressure measurement, measuring the relative pressure difference over the upper airway. To inhale, this pressure must be negative compared with the atmospheric pressure. The diaphragm and rib muscles drive the respiration and the lower that the relative esophageal pressure gets, the more tension is provided by the muscles and more energy is used for respiration.

As measuring of esophageal pressure requires the placement of a catheter or sensor inside the esophageal area, it is an invasive procedure and is not practical for general respiratory measures. Non-invasive methods are useful and popular to measure breathing movements, but these methods do not measure respiratory effort directly. A non-invasive method to measure respiratory effort would be particularly helpful.

For this reason, indirect methods have been developed to evaluate the respiratory effort. One is to use respiratory effort bands or belts, where a sensor belt capable of measuring either changes in the band stretching or the area of and encircled body is placed around the patients' body in one or more places. Typically one belt is placed around the thorax and a second belt is placed around the abdomen to capture respiratory movements caused by both the diaphragm and the rib-muscles. When sensors measuring only the stretching of the belts are used, the resulting signal is a qualitative measure of the respiratory movement. This type of measurement is used, for example, for measuring of sleep disordered breathing and is intended to distinguish between reduced respiration caused by obstruction in the upper airway (obstructive apnea) where there can be considerable respiratory movement measured, or if it is caused by reduced effort (central apnea) where reduction in flow and reduction in the belt movement occur at the same time.

Even if the methods (esophageal pressure measurement vs. respiration movement measurement) differ significantly regarding the signals and units being measured, both are linked indirectly to the actual power used for respiration that is the desired parameter.

Unlike the stretch-sensitive respiratory effort belts, the areal sensitive respiratory effort belts provide detailed information on the actual form, shape, and amplitude of the respiration taking place. If the areal changes of both the thorax and abdomen are known, by using a certain calibration technology, the continuous respiratory volume can be measured from those signals and therefore the respiratory flow can be derived.

The most practical and widely used method to measure respiratory related areal changes is called Respiratory Inductive Plethysmograph or RIP and is explained in details below. RIP technology has been defined as the gold standard respiratory effort signal for accredited Sleep Clinics in the United States for their accuracy, reliability and ease of use.

Respiratory Inductive Plethysmography (RIP) includes the use of respiratory bands to measure respiratory effort related areal changes. RIP technology includes a measurement of an inductance of a conductive belt or belts that encircles a respiratory region of a subject.

The signal amplitude received from the respiratory effort belts depends on both the shape of the subject and the placement of the belts. To create a respiration volume signal by summing the signal of the respiratory effort belts, one must use correct weighting constants for the measured belt signals to transform each signal correctly into a volume signal before summing them together. Further, to perform a quantitative calibration, the signals of the respiratory effort belts must be measured simultaneously with a quantitative reference measure. Known methods therefore require quantitative equipment for respiratory volume measure, such as a spirometer, body-box, or similar ways to measure respiratory volume accurately during the calibration.

Due to the complexity added with using reference respiratory volume equipment and the fact that the weighting constants are subject to change over time with belt and body movements, it would simplify the measurement of respiratory efforts considerably if there were a method available that would evaluate weighting constants without the need of special quantitative equipment for reference measures.

Statistical measures of RIP during normal breathing to evaluate weighting constants may be used for respiratory analysis and sleep diagnostics. However, the calculation of a calibration factor will change if the belts move or the subject changes position. To maintain accuracy, recalibration is needed after such movements and changes, which requires a few minutes of normal, non-obstructive breathing. This can be difficult with a sleeping subject, especially with a subject's suffering from sleep disordered breathing.

A method for calculating and calibrating the respiratory signals in a more continuous fashion without the need for quantitative equipment would be advantageous.

SUMMARY

The present disclosure concerns a method, apparatus, and system for measuring respiratory effort of a subject.

According to one example, the method includes obtaining a thoracic effort signal (T), obtaining an abdomen effort signal (A), and obtaining a respiratory flow (F). The thoracic effort signal (T) is an indicator of a thoracic component of the respiratory effort. The abdomen effort signal (A) is an indicator of an abdominal component of the respiratory effort. The method further includes determining the respiratory effort by adjusting the components of a model of the respiratory system based on the thoracic effort signal (T), the abdomen effort signal (A), or the respiratory flow (F) or any combination of the thoracic effort signal (T), the abdomen effort signal (A), and the respiratory flow (F).

According to another embodiment, a method of measuring respiratory effort of a subject is provided. The method includes obtaining a thoracic effort signal (T) and obtaining an abdomen effort signal (A). The thoracic effort signal (T) is an indicator of a thoracic component of the respiratory effort. The abdomen effort signal (A) is an indicator of an abdominal component of the respiratory effort. The method further includes determining a weighted sum (S) of the thoracic effort signal (T) and the abdomen effort signal (A) that correctly represents the respiratory volume by the relative contribution of the thoracic effort signal (T) and the abdomen effort signal (A) to two or more harmonics of the weighted sum (S).

According to another example, a respiratory effort measuring system is provided, which includes a first sensor device configured to obtain a thorax effort signal (T), a second sensor device configured to obtain an abdomen effort signal (A), and a processor configured to receive the thorax effort signal (T) and the abdomen effort signal (A). The thorax effort signal (T) is an indicator of a thoracic component of the respiratory effort. The abdomen effort signal (A) is an indicator of an abdominal component of the respiratory effort. The processor is further configured to obtain the thorax effort signal (T), obtain an abdomen effort signal (A), obtain a respiratory flow (F) of the subject, and determine the respiratory effort by adjusting the components of a model of the respiratory system based on the thoracic effort signal (T), the abdomen effort signal (A), or the respiratory flow (F) or any combination of the thoracic effort signal (T), the abdomen effort signal (A), and the respiratory flow (F).

According to another example, a hardware storage device is provided having stored thereon computer executable instructions which, when executed by one or more processors, implement a method of measuring respiratory effort of a subject. The method includes obtaining a thoracic effort signal (T), obtaining an abdomen effort signal (A), and obtaining a respiratory flow (F). The thoracic effort signal (T) is an indicator of a thoracic component of the respiratory effort. The abdomen effort signal (A) is an indicator of an abdominal component of the respiratory effort. The method further includes determining the respiratory effort by adjusting the components of a model of the respiratory system based on the thoracic effort signal (T), the abdomen effort signal (A), or the respiratory flow (F), or any combination of the thoracic effort signal (T), the abdomen effort signal (A), and the respiratory flow (F).

DETAILED DESCRIPTION OF VARIOUS EMBODIMENTS

Respiratory Inductive Plethysmography (RIP)

Non-invasive methods to measure breathing movements and respiratory effort may include the use of respiratory effort bands or belts placed around the respiratory region of a subject. The sensor belt may be capable of measuring either changes in the band stretching or the area of the body encircled by the belt when placed around a subject's body. A first belt may be placed around the thorax and second belt may be placed around the abdomen to capture respiratory movements caused by both the diaphragm and the intercostal-muscles. When sensors measuring only the stretching of the belts are used, the resulting signal is a qualitative measure of the respiratory movement. This type of measurement is used, for example, for measurement of sleep disordered breathing and may distinguish between reduced respiration caused by obstruction in the upper airway (obstructive apnea), where there can be considerable respiratory movement measured, or if it is caused by reduced effort (central apnea), where reduction in flow and reduction in the belt movement occur at the same time.

Unlike the stretch-sensitive respiratory effort belts, areal sensitive respiratory effort belts provide detailed information on the actual form, shape and amplitude of the respiration taking place. If the areal changes of both the thorax and abdomen are known, by using a certain calibration technology, the continuous respiratory volume can be measured from those signals and therefore the respiratory flow can be derived.

Figure 1A:
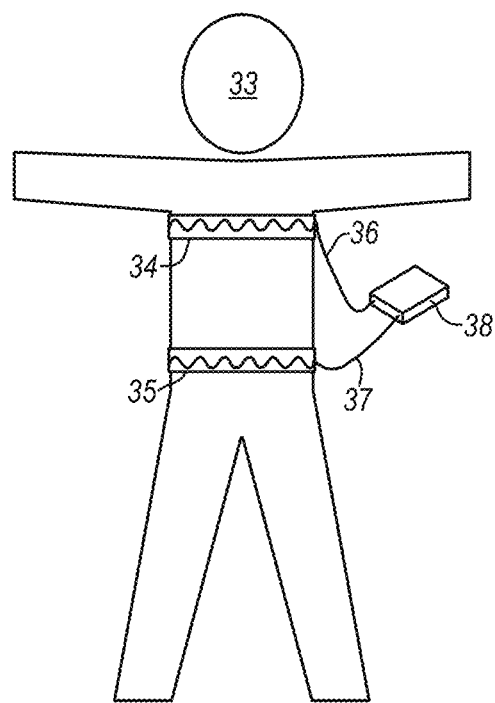
FIGS. 1a and 1b illustrate an example of respiratory inductance plethysmograph (RIP) belts, 1a shows an example of the wave-shaped conductors in the belts, 1b shows the cross-sectional area of each belt, which is proportional to the measured inductance.
Figure 1B:
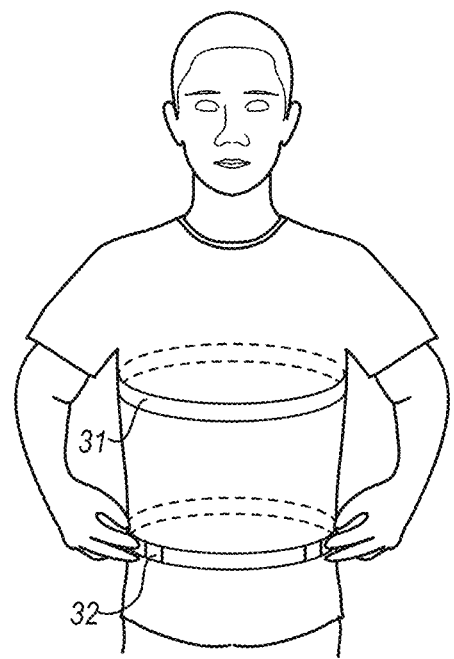
Figure 2:
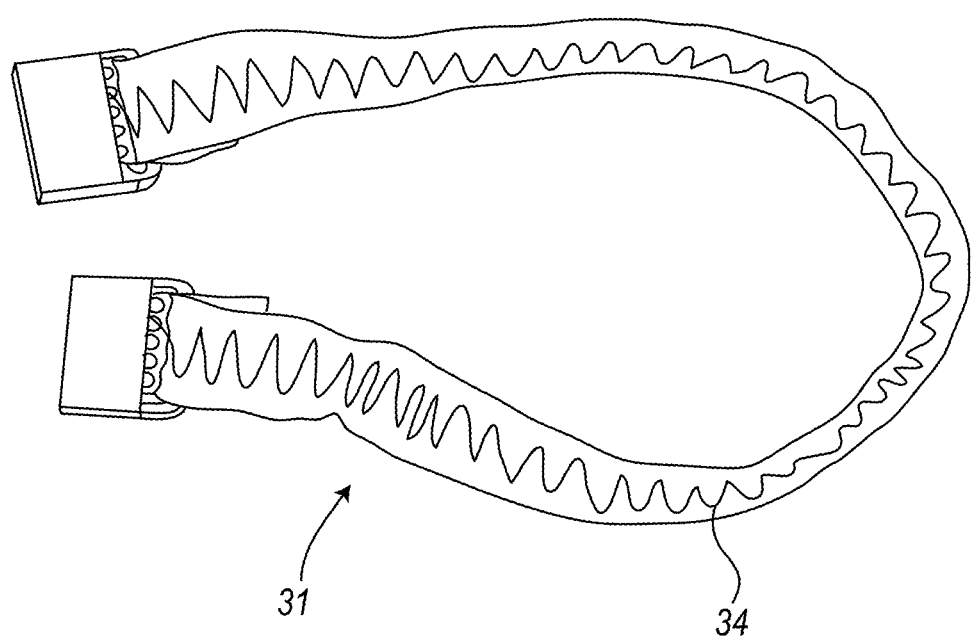
FIG. 2 illustrates an embodiment of an RIP belt.

Respiratory Inductive Plethysmography (RIP) is a method to measure respiratory related areal changes. As shown in FIGS. 1a and 1b, and 2, in RIP, stretchable belts 31, 32 may contain a conductor 34, 35 that when put on a subject 33, form a conductive loop that creates an inductance that is directly proportional to the absolute cross sectional area of the body part that is encircled by the loop. When such a belt is placed around the abdomen or thorax, the cross sectional area is modulated with the respiratory movements and therefore also the inductance of the belt. Conductors 34, 35 may be connected to signal processor 38 by leads 36, 37. Processor 38 may include a memory storage. By measuring the belt inductance, a value is obtained that is modulated directly proportional with the respiratory movements. RIP technology includes therefore an inductance measurement of conductive belts that encircle the thorax and abdomen of a subject.

In another embodiment, conductors may be connected to a transmission unit that transmits respiratory signals, for example raw unprocessed respiratory signals, or semi-processed signals, from conductors to processing unit. Respiratory signals or respiratory signal data may be transmitted to the processor by hardwire, wireless, or by other means of signal transmission.

Resonance circuitry may be used for measuring the inductance and inductance change of the belt. In a resonance circuit, an inductance L and capacitance C can be connected together in parallel. With a fully charged capacitor C connected to the inductance L, the signal measured over the circuitry would swing in a damped harmonic oscillation with the following frequency:

$$f = \frac{1}{2\pi\sqrt{LC}}, \quad (1)$$

until the energy of the capacitor is fully lost in the circuit's electrical resistance. By adding to the circuit an inverting amplifier, the oscillation can however be maintained at a frequency close to the resonance frequency. With a known capacitance C, the inductance L can be calculated by measuring the frequency f and thereby an estimation of the cross-sectional area can be derived.

Figure 3:
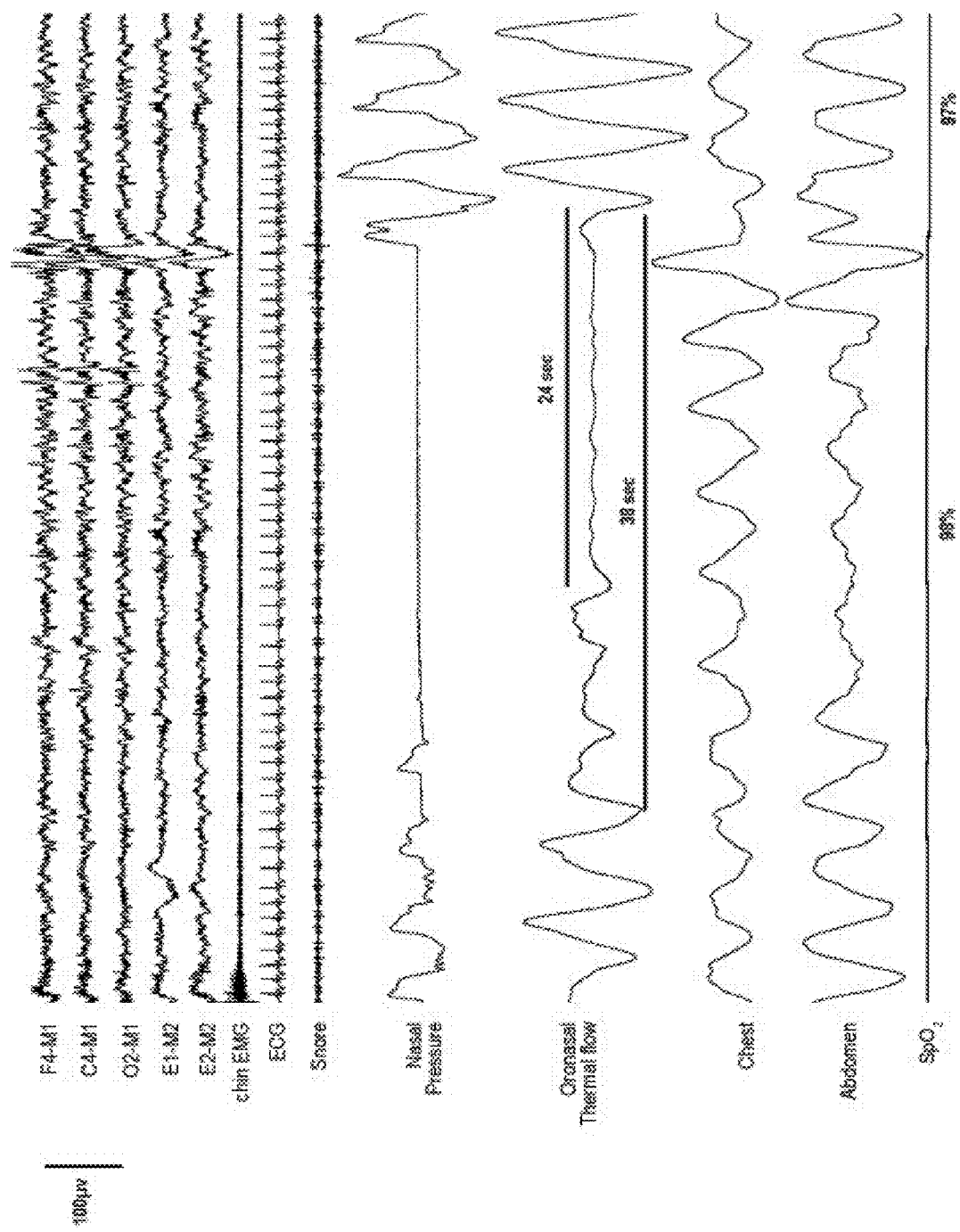
FIG. 3 an example of RIP signals of many recorded signals during polysomnography recording used in the field of sleep medicine. The Chest (Thorax) and Abdomen signals above are typical RIP signals.

FIG. 3 shows a sample of RIP signals obtained using an RIP system described above. As can be seen in FIG. 3, the RIP signals are only two of the many signals recorded during standard polysomnography recording used in the field of sleep medicine. The chest (thorax) and abdomen signals (so labeled) of FIG. 3 are typical RIP signals.

Calibration of RIP Signals

The signal amplitude received from the respiratory effort belts depends on both the shape of the subject and the placement of the belts. The thorax respiration signal may be approximately the same for the whole thorax region but the areal change may be differently proportional to the thorax respiration signal, depending on where on the thorax the belt is placed and how the subject is shaped.

The same may be true for the abdomen region. The abdomen respiration signal may be driven by the diaphragm alone and therefore may be the same all over the abdomen region, but depending on where the belt is located and the shape of the abdomen, the areal change may be differently proportional to the abdomen respiration signal.

Figure 4:
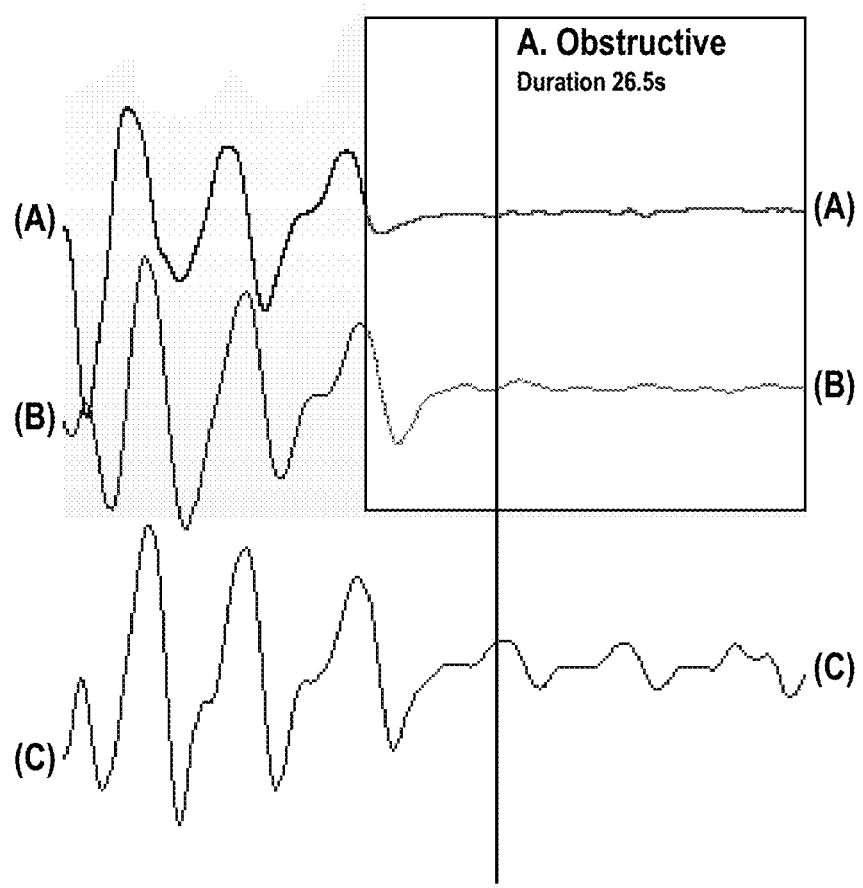
FIG. 4 illustrates a reference flow signal (top, (A)), a flow signal from calibrated RIP sum (middle, (B)), and flow signal derived from uncalibrated RIP signals (bottom, (C)).

To create a respiration volume signal by summing the thorax respiration and abdomen respiration, one must use the correct weights for the measured belt signals to transform each signal correctly into a volume signal before summing them together. FIG. 4 shows a flow reference signal (top, (A)), a flow signal derived from calibrated RIP sum (middle, (B)), and a flow signal derived from un-calibrated RIP signals (bottom, (C)). FIG. 4 further shows an obstruction of a duration of 26.5 seconds.

If the thorax RIP signal is T and the abdomen RIP signal is A the total volume signal can be represented as:

$$V_R = k_v(k_t \times T + (1-k_t) \times A) \quad (2),$$

where $k_t$ is the weight of the thorax signal towards the abdomen signal and the $k_v$ is the gain required to change the weighted belt sum to the actual $V_R$ measured in liters or other volume unit.

To perform a quantitative calibration, the signals T and A must be measured simultaneously with a quantitative reference measure of $V_R$. Based on the result, the constants, $k_v$ and $k_t$ can be derived using methods such as, for example, least square fitting. This method does therefore require quantitative equipment for respiratory volume measure, such as a spirometer, body-box or similar ways to measure $V_R$ accurately during the calibration.

Even if the quantitative measure of $V_R$ is of interest, for example, for pulmonary function tests, it is sufficient for many applications to derive a signal that is only proportional to the actual volume. This is the case in sleep monitoring, where the purpose of the measuring is to detect abnormal breathing patterns, generally by determining if the amplitude of one breath deviates from a reference breath, which would indicate an obstruction of flow. In this case it is sufficient to evaluate the proportion between the thorax and abdomen signals before summing, that is, for a volume proportional sum $V_{S1}$, $$V_{S1} = (k_T \times T + (1-k_T) \times A) \quad (3).$$

Due to the linearity of the system, as the absolute gain of the signal may not be relevant, the weight factor for T can be changed to any value as long as the weight factor for A is changed proportionally. A simplified presentation of the above equation can therefore be used for the sake of argument, where $k_T = 1$ and $k_A = (1-k_T)/k_T$ resulting in the equation:

$$V_S = (T + k_A \times A) \quad (4.1).$$

Due to the complexity added with using reference respiratory volume equipment and the fact that the $k_A$ is a subject to change over time with belt and body movements, it would simplify the measure considerably if there would be a method available that would evaluate $k_A$ without the need of a special equipment for reference measures.

A method may use statistical measures of RIP during normal breathing to evaluate $k_A$, using an algorithm referred to as Qualitative Diagnostic Calibration (QDC), as described in "Calibration of respiratory inductive plethysmograph during natural breathing" by Marvin A. Sackner and his collages. (Sackner M A, Watson H, Belsito A S. J Appl Physiol 1989; 66: 410-420), which is herein incorporated by reference in its entirely.

The QDC algorithm allows a qualitative calibration of the RIP signals during normal breathing to estimate the $k_A$ without the use of a reference volume signal. The method is based on the findings that during normal breathing (non-obstructive), the variance in the amplitude of the thorax and abdomen RIP signals, when correctly calibrated should be the same, given that the tidal volume of the breaths are approximately the same. By measuring a number of breaths (e.g. for a 5 minute period), selecting the breaths that are close to being normal distributed around the average tidal volume, and calculating the standard deviation of the selected breaths for the thorax signal (Sd(T)) and abdomen signals (Sd(A)), the gain factor can be evaluated as follows:

$$k_A = -\frac{Sd(T)}{Sd(A)}. \quad (5)$$

This method may be useful for respiratory analysis and sleep diagnostics. The drawback is however that the gain factor $k_A$ will change if the belts move or the subject changes position. To maintain accuracy, recalibration is needed after such movements and changes, and that requires a few minutes of normal, non-obstructive breathing. This can be difficult with a sleeping subject, especially with a subject's suffering from sleep disordered breathing. Preferably, a calibration factor for the respiratory signals would be obtainable in a more continuous fashion.

As explained above, it is problematic to use QDC calibration for sleeping patients due to the changes in the calibration constant that can be expected through the night, due to movements of the belts and changes of patient body position. The means that have been used to minimize those effects are mainly to use belts that are fixed to the patient by the use of adhesive/sticky materials or woven into the patients clothing. The calibration is then performed in different positions before the sleep onset time. The position is constantly monitored and used to select the most likely calibration gain factor for each period.

Even if this type of adaptive calibration is more accurate than using RIP belts that can move and a single point calibration, it would be beneficial if a method would allow calibration to take place at any time during the night, not requiring normal and non-obstructive breathing periods.

The thorax and abdomen RIP signals contain information on the total areal change of the rib cage and abdomen area. During open airway, the movements are close to synchronized and both signals are similar in shape to the actual respiratory volume signal. This is the condition required for QDC calibration as described above. During total obstruction of the airway, the respiratory volume can be approximated to be close to zero and the sum of the belts should therefore be close to zero as well in a calibrated system. This is the condition required for the Isocal method, where A and T are forced to equal zero by asking the patient to perform an iso-volume maneuver, as described by K. Konno, J. Mead, Journal of Applied Physiology, 1968, Vol. 24, n. 4, 544-548, which is herein incorporated by reference in its entirely. Natural breathing during sleep is however partially obstructed most of the time, making the use of the previously described methods, which are limited for most of the time.

The Components of Breathing

A different model is described herein that describes the respiratory movements of the thorax and abdomen and their relationship with the respiratory volume Vs inhaled at any given time. The respiratory movement of thorax and abdomen may be divided each into two signal components. One holds the movement that is driving the respiration and contributing partially to the respiratory volume. This component is referred to as "the volume-contributing component" or the "real" component. The other contains the rest of the movement that is not contributing any respiratory volume and is referred to as the "paradoxical component" or (P).

The underlying model and parameters of a preferable method are herein described. For a calibrated system the following applies:

From equation (3) above, the following can be derived:

$$i) \quad V_S = (T + k_A A) \quad (3.2),$$

As explained above, due to the linearity of the system, other weight factors for $k_T$ and $k_A$ have the same effect, such as choosing to set the weight factor $k_A$ to be equal to one ($k_A = 1$), arriving at equation (3.3) below, and $k_T$ may be determined as the weight factor, which may be defined as the ration of weights for T towards A.

$$V_{S2} = (k_T T + A) \quad (3.3),$$

Furthermore, both thorax and abdomen could have weights other than 1 resulting in:

$$V_{Sw} = (k_T T + k_A A) \quad (3.4),$$

For ease in understanding the model, in the description below, the weight factor $k_T$ is, however, chosen to be equal to one ($k_T = 1$). Based on equation (3.2), the following may be further defined:

$$T = k_{VT} \times V_S + P \quad (6),$$

$$k_A A = (1 - k_{VT}) \times V_S - P \quad (7).$$

In the above formulas $k_{VT}$ is the contribution of the thorax movement, in the range from 0 to 1 to the volume sum $V_S$, whereas the remaining contribution of $(1-k_{VT})$ must come from the abdomen movement. The product of $k_{VT} \times V_S$ is therefore the flow-contributing component of T while $(1-k_{VT}) \times V_S$ is the flow-contributing component of A. The residual movement of the thorax, T may be termed herein as a paradox component P and is the exact opposite of a paradox movement in $k_A A$. Therefore by summing the two, the P and −P cancel the effect of each other, as this movement is not contributing any respiratory volume.

In the extreme case of almost non-obstructive breathing, the P is close to zero and the shape of both T and $k_A A$ is close to being identical to $V_S$, $$T = k_{VT} \times V_S \text{ and } k_A A = (1 - k_{VT}) \times V_S.$$

During the other extreme case of fully obstructive breathing, $V_S$ drops to zero, T=P while $k_A A = -P$.

The model may therefore successfully describe respiratory movements of thorax and abdomen for differing levels of obstruction, given that the coefficients, $k_A$ and $k_{VT}$ are known. Further, a calibration factor for calibrating the thorax effort signal T and the abdomen effort signal A may be obtained based on the optimized weight factor $k_A$. The weight factor coefficients $k_A$ and $k_{VT}$ may then be stored, and the calibrated thorax effort signal T and the abdomen effort signal A and the volume sum $V_S$ may be stored and displayed on a display device.

From equations (6) and (7) an equation for the parameter P can be derived:

$$T - k_A A = k_{VT} \times V_S + P - ((1 - k_{VT}) \times V_S - P) \quad (8)$$

$$T - k_A A = 2P + (2k_{VT} - 1) \times V_S$$

$$P = \frac{T - k_A A + (1 - 2k_{VT}) \times V_S}{2}$$

$$P = \frac{T - k_A A + (1 - 2k_{VT}) \times (T + k_A A)}{2}$$

$$P = \frac{2T - 2k_{VT} V_S}{2}$$

$$P = T - k_{VT} V_S.$$

As can be seen in equation (8) above, the paradox signal cannot be determined from the T, $k_A A$ and $V_S$ only but is also a function of the actual volume contribution from each belt $k_{VT}$.

In accordance with the model of this embodiment, there are different ways to suitably determine the coefficients $k_A$ and $k_{VT}$, some examples of which are described herein.

Harmonic vectors calibration is based on the theory that xAb=tcS+P and (1−x)Th=(1-tc)S−P, where S=xAb+(1−x)Th, and P is a paradox and S is the flow. It is assumed that in the frequency domain P and S are out of phase. For example, the frequency domain P and S may be 90 degrees out of phase. The flow contributing parts of xAb and (1−x)Th are in phase and the paradox, non-flow contributing parts P cancel each other when xAb and (1−x)Th are scaled with the correct value of x and added. When the Ab and Th parts are scaled with the correct x value, the P parts are of equal amplitude but opposite signs in the xAb and (1−x)Th. When xAb and (1−x)Th are separated into their frequency components all flow contributing frequency components of zAb and (1−x)Th are parallel to S, it should be seen that when the correct calibration value is chosen that the amplitudes of the parallel components should be the same as in S multiplied by a constant, tc and (1−tc) in xAb and (1−x)Th, respectively. Based on this theory, the respiratory flow (F) of the subject may be obtained by derivation.

A different model is described herein that describes the respiratory movements of the thorax and abdomen and the relationship between the volume-contributing thoracic component (VST) and a thoracic paradox component (PT) of the thoracic respiratory movement, and the volume-contributing abdomen component (VSA) and an abdomen paradox component (PA) of the abdomen respiratory movement. In this model the time series describing the volume-contributing thoracic component (VST) and the time series describing thoracic paradox component (PT) have a 90 degree phase difference between frequency components at identical frequencies. In this model the time series describing volume-contributing abdomen component (VSA) and the time series describing abdomen paradox component (PT) have a 90 degree phase difference between frequency components at identical frequencies. In this model the time series describing thoracic paradox component (PT) and the time series describing abdomen paradox component (PA) have a 180 degree phase difference between frequency components at identical frequencies.

A correct calibration value is found when the amplitude of the thoracic paradox component (PT) equals the abdomen paradox component (PA) at all identical frequencies.

The Characteristics of a Calibrated System

In a correctly calibrated system, the paradox component P is equivalent to, but opposite in amplitude in both thorax and abdomen signals. The paradox is caused by the negative pressure in the thorax during inhalation and is therefore directly affected by the respiratory effort and the level of flow resistance in the upper airway. As the flow resistance is in most cases either caused by soft tissue in the upper airway or enlarged tonsils, it is not constant but is modulated by and during the respiration. The pressure drop over the flow resistance causes the tissues involved to narrow the airway even further during inhalation, but widens again during exhalation.

For this reason the $V_S$ and P signal components may have the following characteristics.

Amplitude and Power Loss Due to Summing of Channels

As $V_S$ is the sum of the volume-contributing components of the thorax and abdomen signals, the paradox components present in T and $k_A A$ disappear in the sum. As part of the signal is lost, the amplitude of the summed signal $V_S$ is therefore less than the sum of the amplitudes of T and $k_A A$, and the same is true for the power of the summed signal $V_S$ as compared to the sum of the powers of T and $k_A A$. (In this context, 'power' refers to mathematical power function, not electrical power.) Thus, based on equation (4.1), $V_S=(T+k_A A)$, it follows that for the amplitude, the following applies:

$$|V_S| \leq |T| + |k_A A| \qquad (9),$$

and therefore its power is as follows:

$$P<V_S> \leq P<T> + P<k_A A>. \qquad (10).$$

This power loss is minimal during normal breathing, increases with increased partial obstruction until it is absolute during complete obstruction. For any given timeframe, the amplitude and power loss are at maximum when the sum is correctly calibrated. Accordingly, a useful $k_A$ value can be obtained, which is a value that maximizes the power loss and/or amplitude loss, compared with the sum of the power or amplitudes respectively, of T and A over a period of time. This is done in certain useful embodiments of the disclosure and readily achieved with iterative calculations.

Paradox Present in Higher Frequencies

Obstructive changes in the airway during a single breath are by nature quicker events than the respiration itself and do therefore contain higher frequency components compared with the flow signal. The power of P is therefore more in the higher frequencies compared with $V_S$ and the relative power of the fundamental frequency is therefore higher in $V_S$ than in both T and $k_A A$.

Accordingly, in some embodiments a useful $k_A$ value is obtained, by finding a $k_A$ value such that the proportional power of lower frequencies in the respiratory signal is maximized as compared with higher frequencies in the respiratory signal, over a period of time. It is apparent that "lower" and "higher" frequencies in this context are determined based on normal breathing frequencies. Thus lower frequencies could be, in one embodiment, frequencies lower than double the average frequency being measured (which is generally the fundamental frequency of the breathing signal, readily determined, e.g. by FT transforming of the signal). Or in other embodiments frequencies lower than 1 Hz, 0.5 Hz or lower, such as lower than 0.2 Hz (12 breathes per minute) or lower than 0.1 Hz. Higher frequencies would accordingly be those frequencies that are higher than the cutoff between lower and higher frequencies, or in some embodiments those frequencies that are higher than the fundamental frequency of the breathing signal.

Based on the above, the present disclosure further provides for, in some embodiments, ways to use the magnitude of the loss of amplitude or power, the magnitude of loss of the higher frequency components or a combination of these to determine a $k_A$ value that is considered optimal over a certain period of time.

Optimization Methods for $k_A$

1. Maximum Fundamental Frequency Optimization (MFF)

In another embodiment, a MFF method seeks by trial and error over a certain period, the $k_A$ that results in the $V_S=(T+k_A A)$ that maximizes the power of the fundamental frequency of the signal relative to the overall signal power. The logic is that as P contains higher frequency components than $V_S$, maximizing the relative power of the fundamental frequency is the same as minimizing the effects of P in the sum.

The MFF method may be applied in useful embodiments. The fundamental frequency is generally the undisturbed breathing rhythm, the period referred to can be relatively short, such as but not limited to breath by breath (one breathing cycle), or a predetermined period such as 1 minute or a few minutes. Different time-frequency analysis methods can be used separately or together for maximizing of the method efficiency, including but not limited to, Wavelet transform, Fourier transformation, statistical modeling, etc.

2. Minimum Signal Amplitude Optimization (MSA)

A MSA method seeks by trial and error for a given period the $k_A$ that results in the $V_S=(T+k_A A)$ that minimizes the resulting signal compared with the amplitude of T and $k_A A$, $$S_l \min = \min\left(\frac{\text{RMS}(V_S)}{\text{RMS}(T) + \text{RMS}(k_A A)}\right). \quad (11)$$

$S_l$ can be understood as relative difference between the $V_S$ amplitude versus the sum of the amplitudes of T and $k_A A$. The logic is that P contributes to the amplitude of the measured signal but not to the amplitude of the respiration. By minimizing the amplitude of the resulting signal $S_l$, one is minimizing the influence of P and the respiration part of the signal is therefore maximized. The period in the MSA method can in some embodiments be the period of a single breath (suitably determined as described above), or a few breaths, or longer, such as in the range from about 10 sec. to about 10 minutes, such as e.g. about 0.5 minute, or about 1 min period, about 5 minutes or about 10 min period. In other embodiments longer periods are used, such as 0.5 hour, 1 hour, or a period of a few hours (e.g. 2, 3, 4 or 5 hours), where a suitable period can be selected depending on the application.

3. Minimum Obstruction Amplitude (MOA) Optimization

The MOA method is useful for periods of time in embodiments where there are quick changes in the signal amplitudes between breaths and periods of obstruction. The obstructive periods provide the opportunity to perform conventional isovolume calibration, by selecting the $k_A$ that minimizes in the best way the $V_S$ during obstruction. This can be done for a period of the signal (e.g. 0.5 minute, or 1 min or a few minutes such as in the range 1-5 minutes), by dividing the period into a number of n shorter time frames of few seconds each (such as e.g. in the range of 3-10 seconds, or in the range of 3-5 seconds; should fit within an apnea). For a given timeframe i, the $S_l \min <i>$ is found and the relative $k_A <i>$ is stored. The value of $k_A$ for the whole period (longer period) is then selected by a weighted average over the period by giving the timeframes that resulted in the lowest $S_l \min$ values the maximum weight. More weight can be given to the timeframes that performed in the best way by using a non-linear weight transformation.

In some embodiments, combinations of two or more of the above methods are applied to obtain a suitable optimal $k_A$ value.

In other embodiments one or more method as described above is applied to derive an intermediate $k_A$ value for a shorter time span, such as e.g. in the range of 5-60 seconds, such as 5-30 seconds, or in the range 5-20 seconds, or in the range 10-30 seconds, and weighing the performance for each timespan and choosing a $k_A$ for the longer timespan (e.g. in the range 1-15 minutes, or in the range 1-10 minutes, such as 5-10 minutes, or longer time spans such as in the range 10-60 minutes, or in some embodiments even longer periods, such as in the range 1-10 hours, e.g. in the range 1-5 hours or in the range 5-10 hours), based on selecting the method providing the most determinant result.

For evaluating and deriving a suitable determinant value of the weighing ratio, various methods can be applied. In one embodiment the performance of the intermediate periods and intermediate values is evaluated by weighing the performance for each intermediate time span (e.g. averaging or otherwise statistically comparing), then the different methods can be compared by comparing which method(s) gives a most consistent value with minimal fluctuations while maintaining the minimal paradoxical components.

Weighting in the Neighboring Periods

The method reliability is in some embodiments enhanced further by selecting a set of periods and basing the selection of $k_{Aj}$ on an average, weighted sum or other performance criteria from the periods in the set. In this way, an accurate $k_{Aj}$ value can be selected for periods that have low signal and frequency magnitude losses, based on a more reliable estimation of a neighboring period.

This is in some embodiments done, e.g., by splitting each minute (or other chosen time span) into overlapping intermediate periods (e.g. 5 seconds, or intermediate periods of other chosen time length, such as but not limited to 3 seconds, 8, or 10 seconds), the $k_{Aj}$ value used for the whole time span can be the weighted sum of the $k_A$ values for each intermediate period where the weight of the periods that have the maximum amplitude/power loss and/or frequency loss is higher than for periods that show lower losses. This can then be applied for longer periods, taking a set of time spans (e.g., minute time spans) and for example calculating a weighted trend-curve for the changes of $k_A$ minute by minute, giving the minutes with the strongest losses the maximum weight and those with low losses the minimum weight.

Selecting the Optimization Method

To adapt optimally to the information available at each period in the signal, the method should preferably use the $k_A$ that fits best for each condition. The measure of how well a method performs can be based on the quantity of the amplitude, signal or frequency loss, where the method providing the highest loss is generally considered the optimal one.

A good criteria for selecting the $k_A$ also preferably results in less switching between methods and optimally that switching from one method to the other occurs when the two methods predict nearly the same value of $k_A$. This way a continuous trend is achieved where sudden shifts in the resulting signal, caused by switching methods, are avoided.

To further optimize the selection criteria, a good result can be achieved by processing a series of periods instead of one by one and then choosing the methods for each period that maximizes the continuity of the $k_A$ between periods, minimizes the number of switches between methods or a combination of both.

Figure 5:
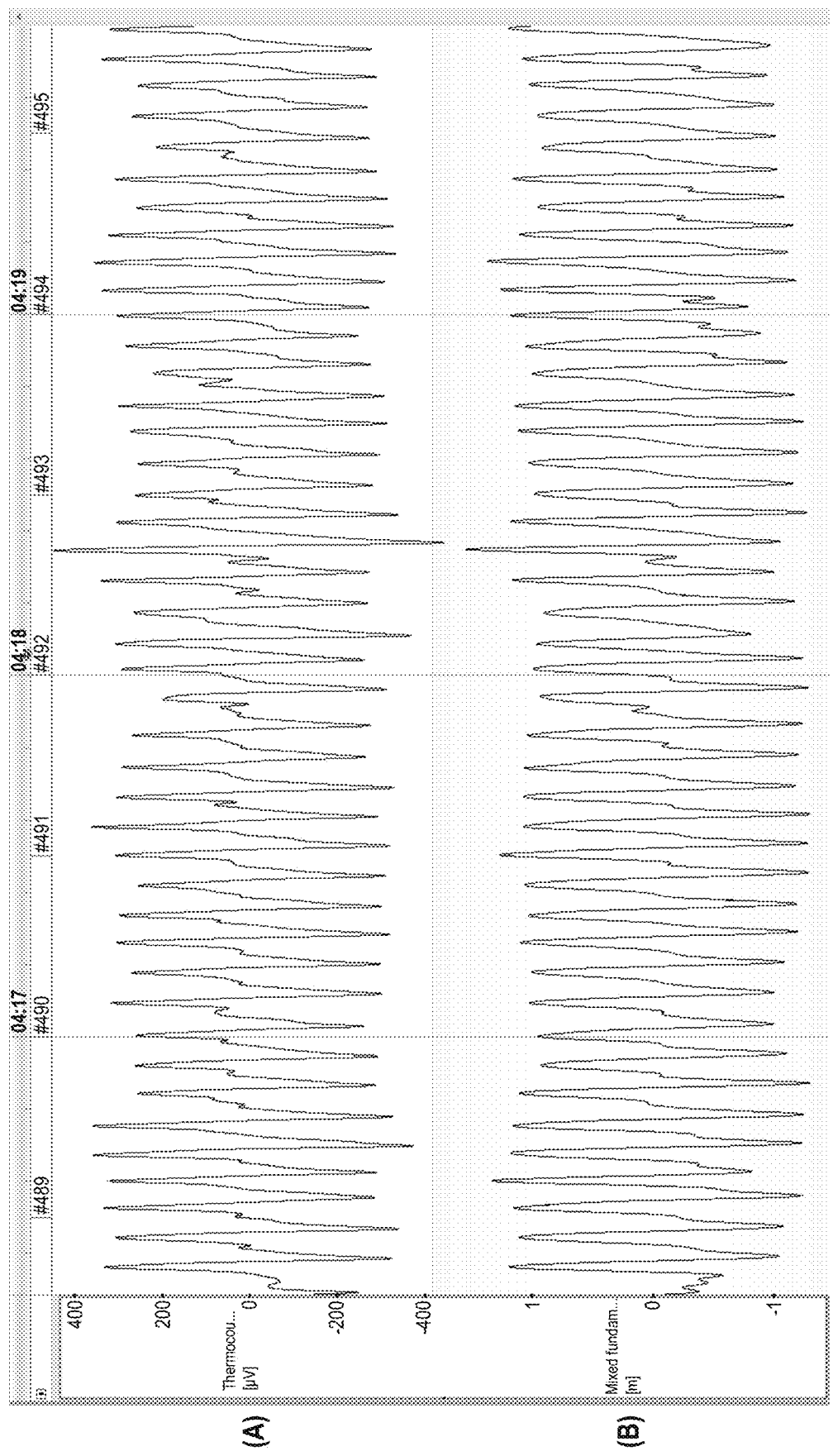
FIG. 5 shows a comparison of reference flow signal of type pneumo flow (top, (A)) compared with flow signal derived from the calibrated RIP sum (bottom, (B)).

FIG. 5 shows a comparison of reference flow signal of type pneumoflow (top, (A)) compared with flow signal derived from the calibrated RIP sum (bottom, (B)).

Figure 6:
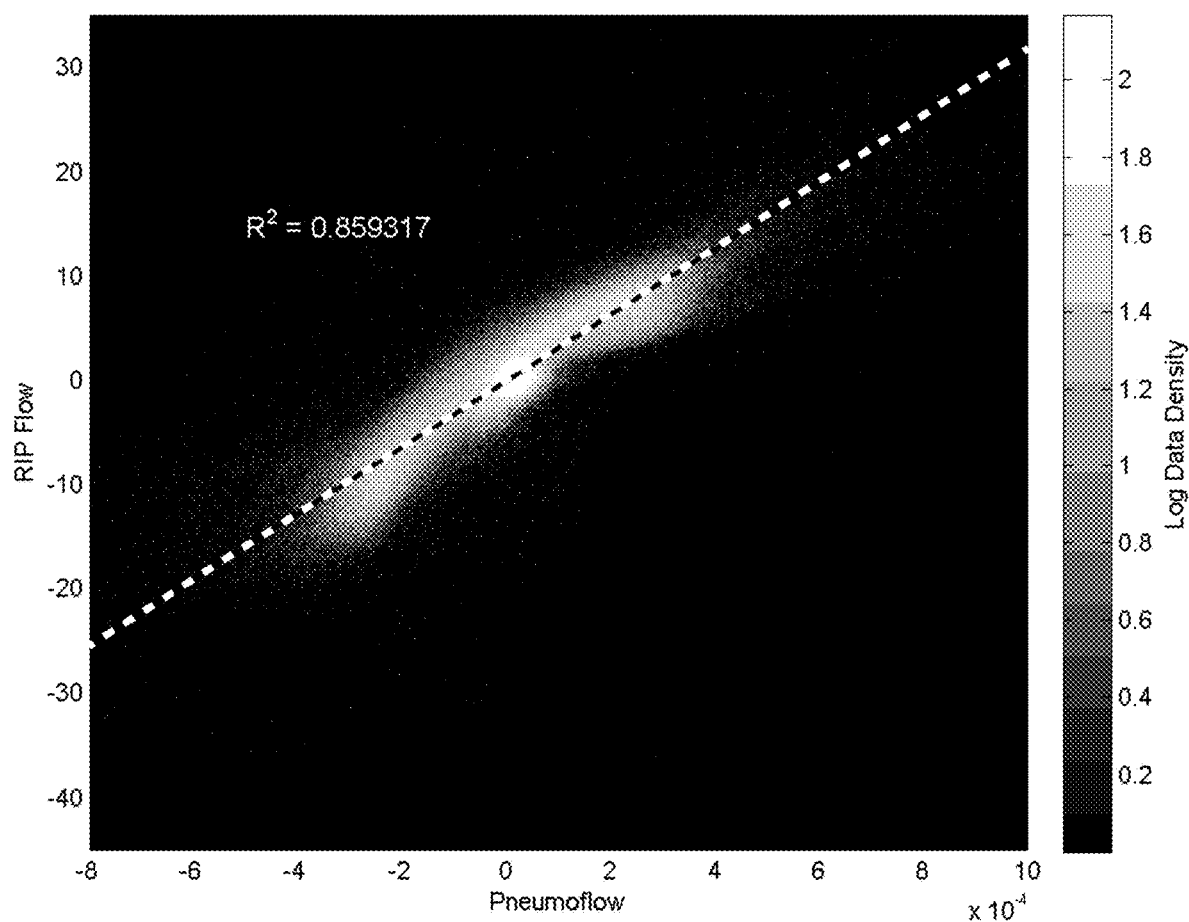
FIG. 6 shows data of a whole night comparison between RIP flow and pneumo flow.

FIG. 6 shows data of a whole night comparison between RIP flow and Pneumoflow.

Signals Derived from the Calibrated Effort

A number of interesting and useful signals can be derived with the embodiments of this disclosure, from the calibrated thorax and abdomen signals.

The Paradox P and the Thorax Volume Contribution $k_{VT}$

As demonstrated in equation (8), even after optimally calibrating the sum, the level of the paradox signal P has more than one solution depending on the $k_{VT}$.

To evaluate the P, a method must be created to seek for the correct $k_{VT}$. The physiological characteristics of P is that the paradox is driven by the pressure difference in the thorax and in the surrounding atmosphere, caused by the inhalation of air over a partial obstruction in the upper airway. For a given pressure difference, the paradox status generally has a balance to the lowest energy level capable of creating that status. This characteristic can be used to determine a useful and correct value P by choosing the $k_{VT}$ that results in the lowest power function/amplitude of P. Accordingly, in a further embodiment, this disclosure provides a method for determining a useful value of the paradox component P.

The paradox signal P is of special interest as it is directly derived from the thorax internal pressure and is a strong indication of the respiratory effort taking place for each breath. This parameter is a candidate for being used as a substitute for a very invasive method currently being used in sleep medicine. This method is a direct measure of the esophageal pressure that is currently performed by threading a catheter through the nose and into the esophageal to monitor the respiratory pressure below the upper airway obstruction.

The other signal is the thorax contribution, which is also of interest as the physiology suggests that the ratio of thorax contribution vs. abdomen contribution changes with the level of sleep, the respiratory muscular activity being different during REM sleep compared with the N1, N2, and N3 sleep stages. Sudden changes in the contribution ratio are therefore strongly related with REM onset and offset.

Figure 7:
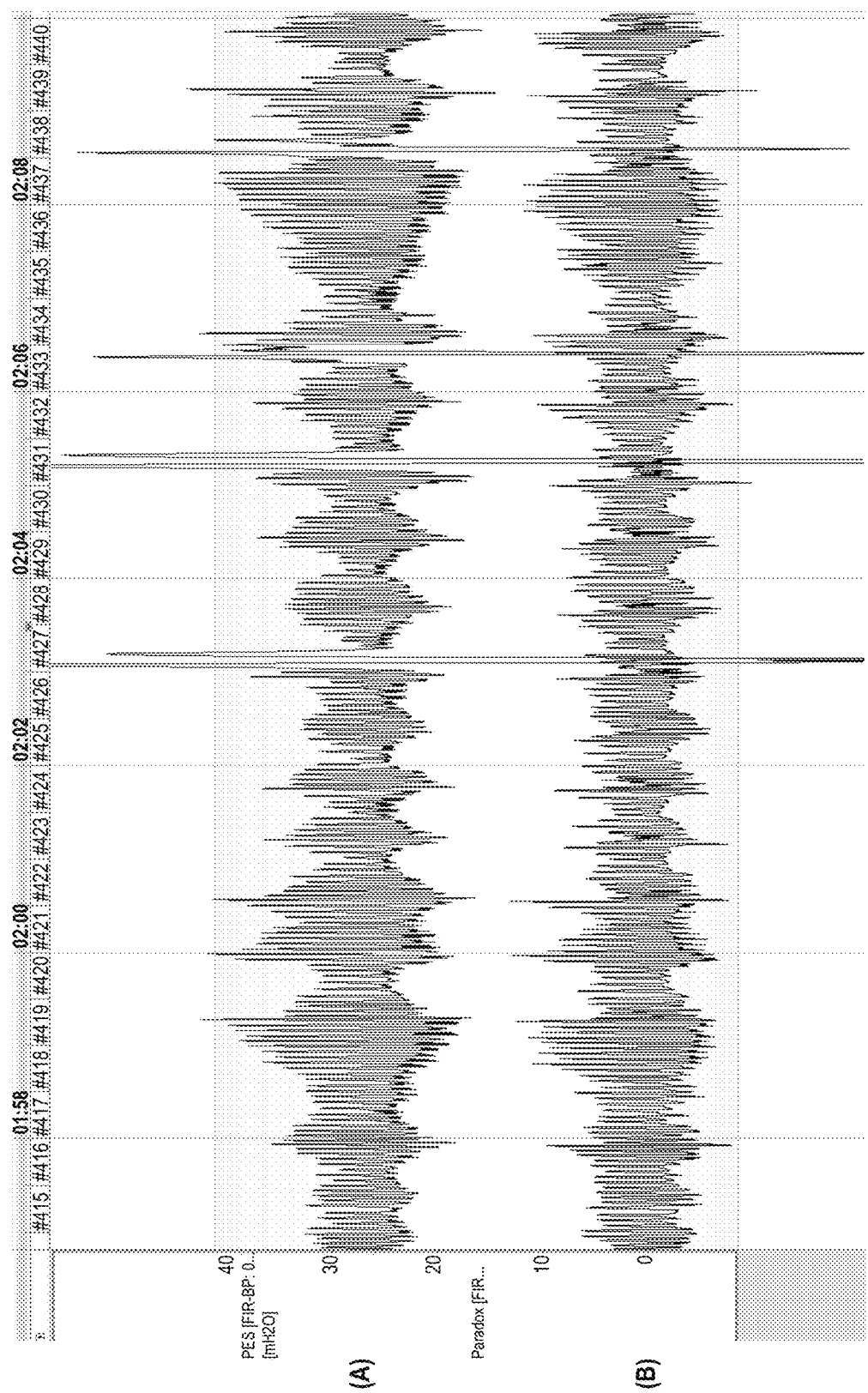
FIG. 7 shows a comparison between measured esophageal pressure (top, (A)) and a non-volume contributing effort signal (bottom, (B)) derived from RIP signals.

FIG. 7 shows a comparison between esophageal pressure (top, (A)) compared with the derived P signal (bottom, (B)).

The Power Loss Ratio

As described in equations (9) and (10) the total amplitude and thus the power of the sum $V_S$ is less than the sum of the amplitude and power of the T and $k_A A$ due to the loss of the paradox signal P.

The value $S_l$min defined in (11) describes the efficiency of the respiration, that is, what portion of the respiratory movement did result in respiratory flow and what portion did not. This index is of great interest as it predicts in a continuous manner the quality of the breathing, being 100% during no obstruction and becoming 0% for total obstruction or, the other way around, the power loss being 0% for no obstruction and 100% for full obstruction.

Figure 8:
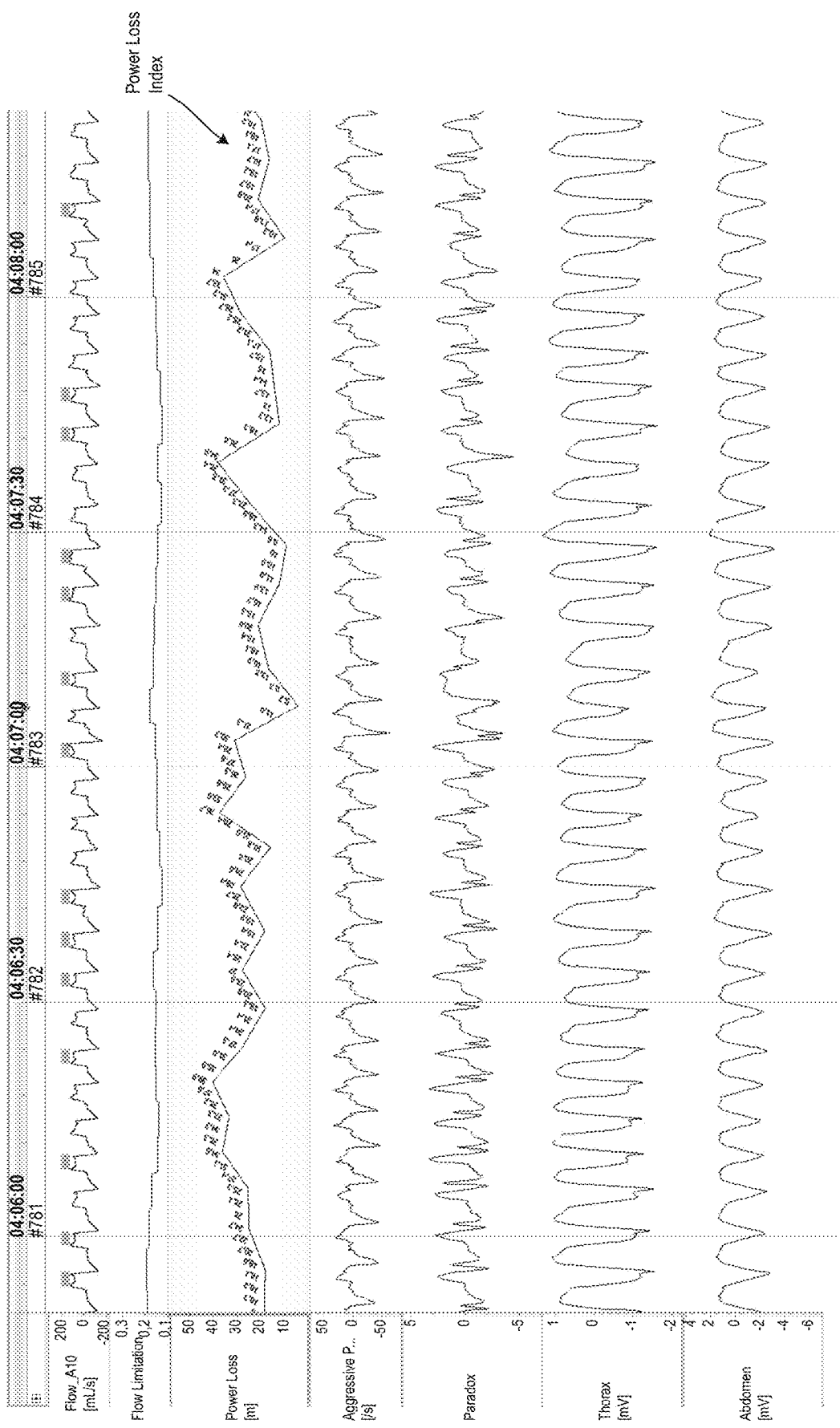
FIG. 8 shows an example of a power loss ratio (annotated) that evaluates in a quantitative manner the effort of breathing.

As this index is the same as is used to seek the calibration value $k_A A$, it can also be calculated directly from the belt signals by applying the model defined in (11), seeking the $k_A$ that results in the minimum $S_l$ min and use that value as a power loss index. FIG. 8 shows a power loss ration evaluated in a quantitative manner the effort of breathing.

Figure 9A:
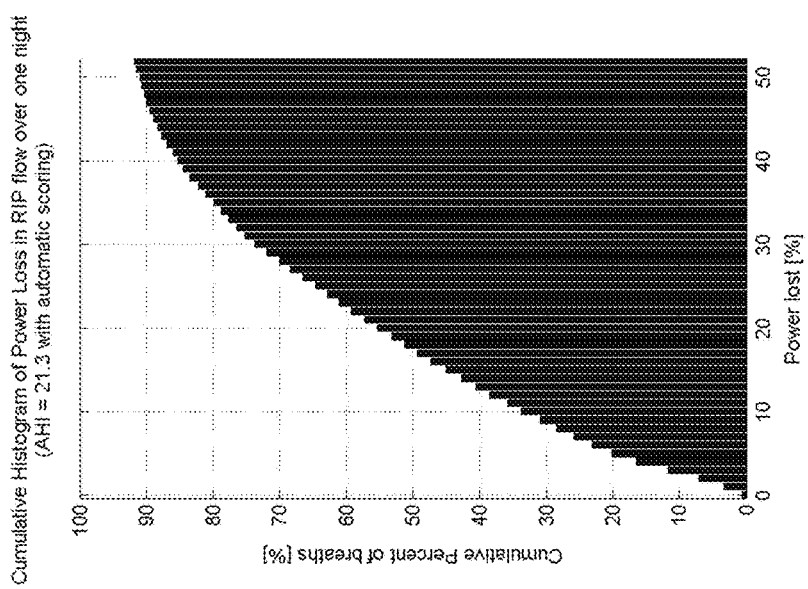
FIGS. 9a, 9b, and 9c, respectively, show a cumulative and relative histograms for power loss in 3 subjects with different levels of upper airway obstruction, from left, (a) subject 1: AHI 0.2, (b) subject 2: AHI 9.8, and (c) subject 3: AHI 21.3.
Figure 9B:
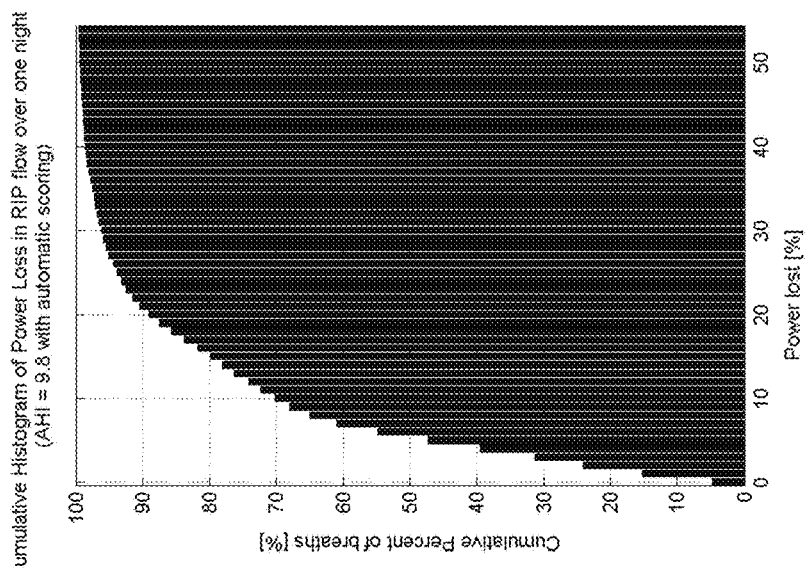
Figure 9C:
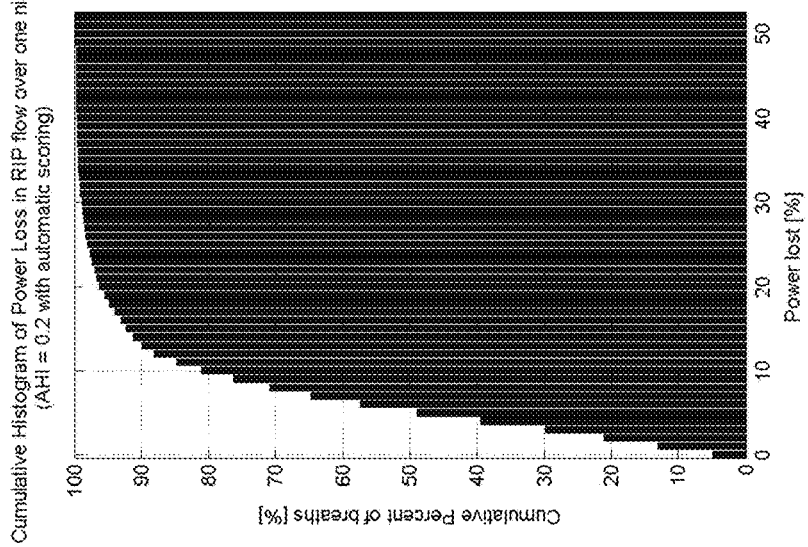

FIGS. 9a, 9b, and 9c show cumulative and relative histograms of power loss in three subjects with different breathing. As can be seen the histograms are quite different, illustrating difference between subjects with healthy breathing and subjects with disordered breathing. Using 20% power loss as a threshold, only 5% of the breaths of Subject 1 are above that threshold, 20% of the breaths of Subject 2 and half of the breaths of Subject 3. The power loss index is therefore a candidate to be used as a quantitative measure of the level of partial obstruction.

Figure 10:
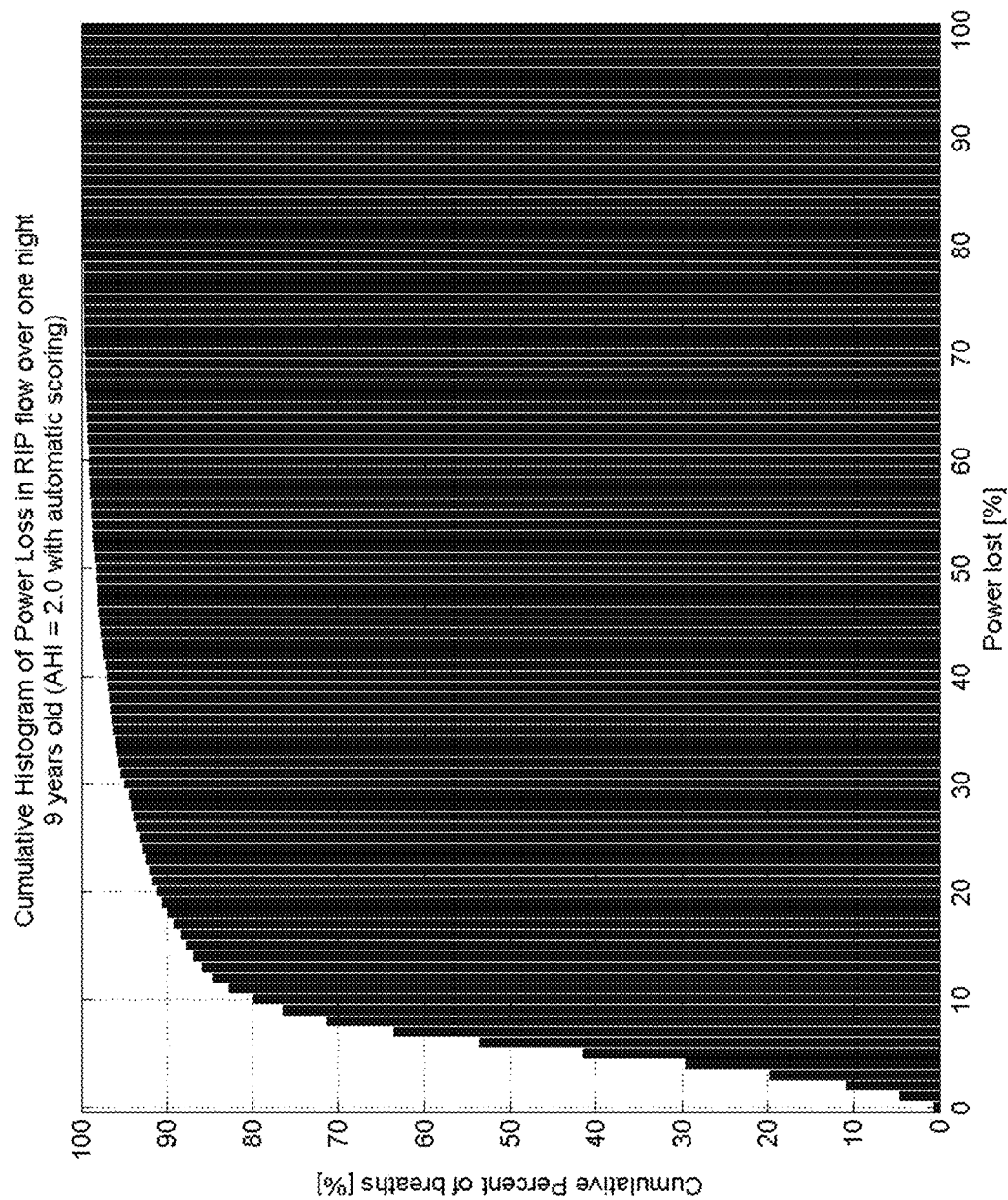
FIG. 10 shows a cumulative histogram of power loss in RIP flow over one night of a 9-year-old patient with AHI of 2.0.

FIG. 10 shows a histogram for a 9-year-old subject with AHI of 2.0. As can be seen on the Histogram from the 9-year-old above with scored level of apneas of AHI 2.0, 10% of his breaths are below the 20% threshold and where as 99% of Patients 1 breaths are below 30% signal loss, more than 5% of the breaths of this 9-year-old are above the 30% signal loss limit or more than measured in Patient 2 with AHI of 9.8.

The power loss index is therefore a candidate to be used as a quantitative measure of the level of partial obstruction.

Volume Calibration and Stabilization

As can be seen from equations (2) and (3), $V_R$ is an absolute volume signal measured in liters, while $V_S$ is a signal that is directly proportional to $V_R$ but is not the absolute volume signal. If the sensitivity of T changes in (3) due to belt movement or other changes in physiology, the gain between $V_S$ and $V_R$ changes during the night. This causes the problem for signal like the $V_S$ and P that even if their initial values where known in a volume unit like liters, they would change or drift through the night. This can be prevented to some degree by fixing the belts as tightly to the subject as possible. However, if there were a biomedical parameter that would allow the belts to be regulated to show a constant ratio towards $V_R$, the results would allow the signals to be used with confidence to compare amplitudes at different times over the night.

The present disclosure provides a further method that makes use of the physiological characteristics that the human body regulates the intake of oxygen to match the need of the cells at all time, not building up or dropping oxygen levels during normal breathing. The indication of increased metabolism is higher minute ventilation (minute ventilation referring to the total volume inspired or expired per minute) and heart rate and during aerobic breathing the ratio between minute ventilation and heart rate is close to linear. The method monitors the relative minute ventilation from the $V_S$ signal and compares it to a measured heart rate. The characteristic linearity between the minute ventilation and heart rate is captured during periods where the $k_A$ is not changing significantly but where there is a variation in the minute ventilation and heart rate. The captured value is then used to correct the $V_S$ when there is a change in the $k_A$ values. This way the $V_R/V_S$ ratio can be kept nearly constant throughout the recording, allowing volume calibration to take place at one or more points during the recording and delivering reliable measure for all periods.

Time Variance

Even with the above-described model for calibration and effort measurements within a certain timeframe, a complete model of respiration during sleep may to take into account more variables that affect both the accuracy of the calibration and the respiratory effort measure. Parameters such as time-variability of intercostal muscle activity and different body pressure on the respiratory system with different body positions can have a significant effect on the respiratory effort measure and calibration values. Below is described the effect of those variables on the measure and how it is possible to correct for the influence by including more information on the respiration to the model.

1. Improved Accuracy Respiratory System Model for Sleep

Figure 11:
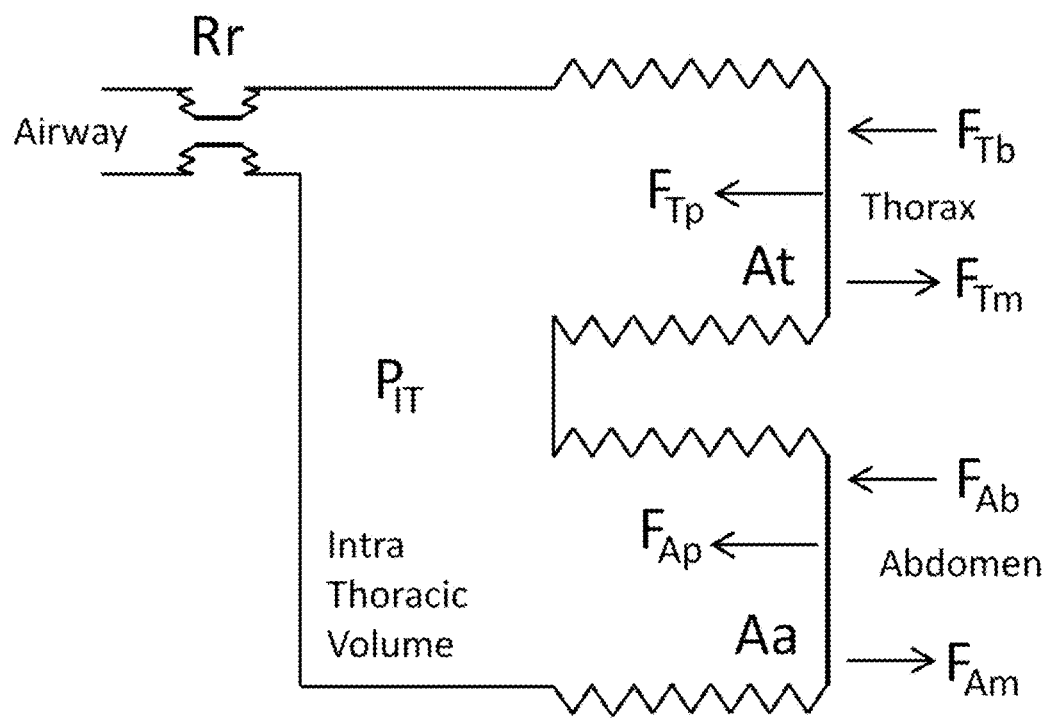
FIG. 11 shows a multi-parameter respiratory system model for sleep.

In FIG. 11, a multi-parameter model can be seen showing some key parameters of the respiratory movement. The airway goes from a subject's mouth and nose, through airway resistance Rr into the intra thoracic volume. The inner pressure of the intra thoracic volume PIt is caused by the pressure drop over airway resistance Rr during inhalation and exhalation. Airway resistance Rr may be considered a time-dependent variable modulated by the respiratory flow that depends on body and head position, muscle tonus of the upper airway, basic diameter of airway and tongue position. The thorax area (At) and abdomen area (Aa) movements are driven by the intercostal muscle providing force FTm and the diaphragm providing force FAm. For a respiratory movement to start, the thoracic and diaphragm muscle force must overcome any counter forces from the body. For the thorax, the counterforce FTb is caused by lifting the chest weight and stretching muscle and skin of the chest. For the abdomen, the diaphragm must overcome the counter force FAb created by the organ hydraulic pressure from the abdomen.

Figure 12:
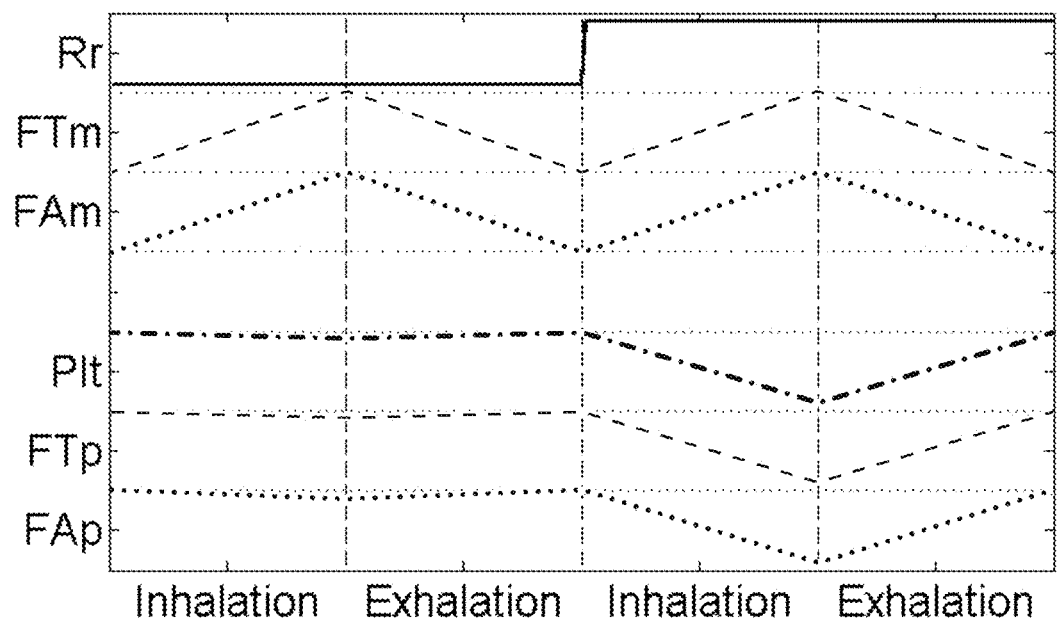
FIG. 12 graphically shows a first scenario according to the model of FIG. 11.

As shown in a first scenario in FIG. 12, when inhalation starts, the intrathoracic pressure PIt depends on the flowrate and the flow-resistance in the airway Rr. PIt may be considered negative during inhalation, causing air to flow into the lungs. This negative pressure causes an additional force on the thorax and abdomen (FTp and FAp), where:

$$F_{Tp} = PIt * At, \text{ and}$$

$$F_{Ap} = PIt * Aa.$$

From the model above, according to a first scenario, low Rr results in low PIt, and low PIt results in low FTp and low FAp. High Rr results in high PIt, resulting in high FTp and high FAp.

2. Reflecting the Respiratory Effort Measure in the New Respiratory Model

Figure 13:
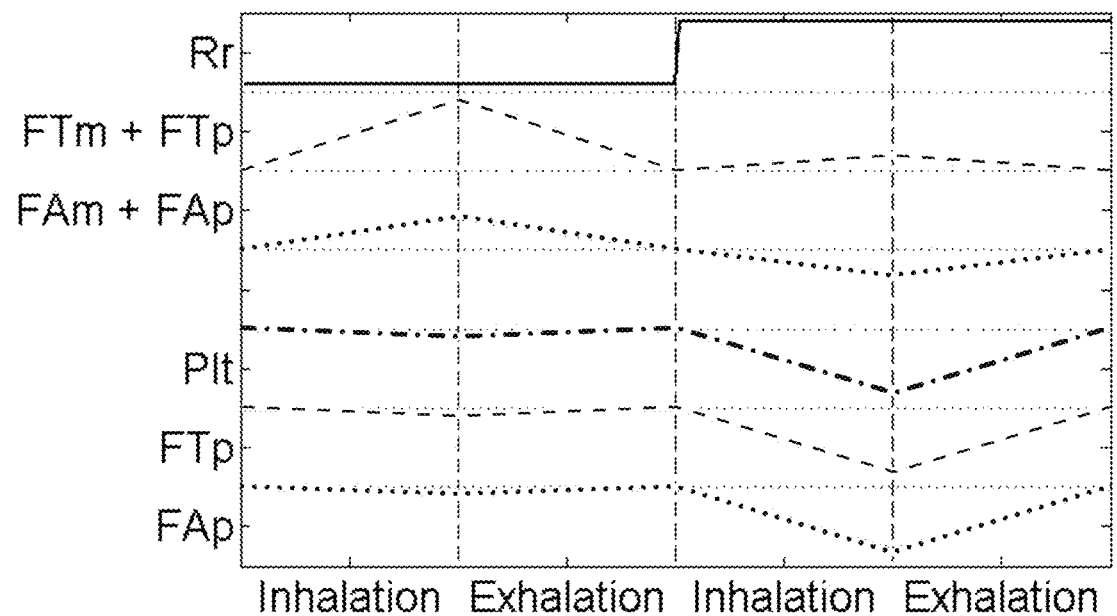
FIG. 13 graphically shows a second scenario according to the model of FIG. 11.

From the model above, it can be understood how the power loss algorithms are related to the effort measured by the intrathoracic pressure PIt. Referring to a second scenario shown in FIG. 13, if it is assumed that for a certain amount of time, the patient is not changing position giving constant FTb and FAb, and the ratio of his thorax respiratory drive FTm towards his abdomen respiratory drive FAm is close to constant.

Now if it is assumed that the Rr is very low, that is the upper airway resistance is negligible. This means that there is no PIt buildup—or close to no PIt buildup—and therefore FTp and FAp are close to or equal to zero. In this system, the thorax and abdomen move in synchrony but independently, that is, the movement of one does not affect the other. The result is that there is no power loss correctly predicting very low PIt and low respiratory effort.

Now if it is assumed that Rr is very high during inhalation, causing the upper airway to collapse. In this situation, any thorax or abdomen movement causes a change in intrathoracic pressure PIt that is proportional to the movement. If the total force of either the thorax or abdomen gets to be negative during inhalation, (FTm−FTb−FTp)<0 or (FAm−FAb−FAp)<0, the one with the negative value being drawn inwards while the other moves outwards, creating 180° phase shift between the belts or paradox breathing. In this case, the power loss in a correctly calibrated system is 100%, correctly describing the high intrathoracic pressure PIt.

According to the second scenario, FAm<FTm. When Rr is low both FTm+FTp>0 and FAm+FAp>0. When Rr is large FTp and FAp become large resulting in FTm+Ftp>0 and FAm+FAp<0.

Figure 14:
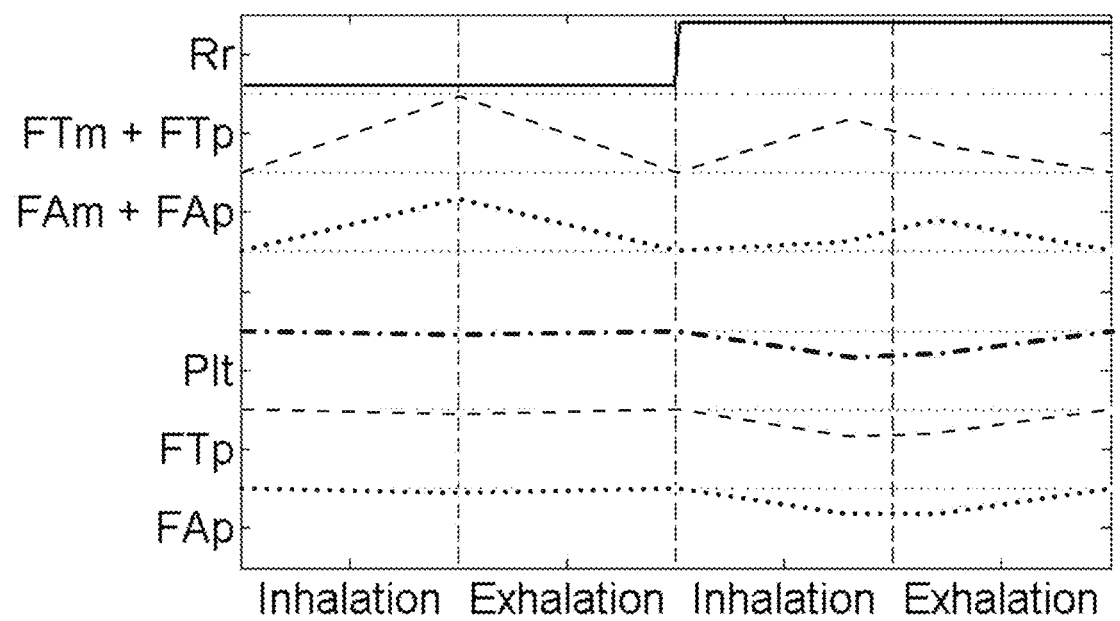
FIG. 14 graphically shows a third scenario according to the model of FIG. 11.

The third scenario, as shown in FIG. 14, would be a partial closure during inhalation with medium value of Rr. In this case, considerable PIt could build up, but both (FTm−FTb−FTp)>0 and (FAm−FAb−FAp)>0. This means that both parts move outwards during exhalation, but the stronger one will lead the movement while the other is held back. The one leading will delay the one following from reaching his maximum value and the follower will first reach maximum when the leader has started exhaling. This causes both a phase shift and loss of power where the squared sum of the traces is lower than the sum of the square sums of each trace. This will result in a power loss value somewhere in the range of 0-100% depending on the level of the loss. For fixed FTm, FTb, FAm and FAb, the loss is only dependent on FTp and FAp, eventually only dependent on the PIt. The power loss correctly delivers a value directly proportional to the PIt as it is supposed to.

According to the third scenario, FTm>FAm, causes Thorax to rise faster than Abdomen due to the fact that FTm+FTp>FAm+FAp.

3. Time Variables Derived from the Respiratory Model

Over longer periods of time, the FTm, FTb, FAm and FAb are not constant but may vary. The force from the body pressure, FTb and FAb is significantly dependent on the body position.

In supine position, the abdomen full weight causes pressure on the diaphragm resulting in high FAb while the thorax may move relatively freely causing lower FTb. With the body lying on either side, there is a significant pressure on one side of the thorax, increasing the FTb while the abdomen is now on level with the diaphragm, causing lower FAb. Prone position of the body will cause pressure on the thorax, causing high FTb while it depends on the circumference of the Abdomen if the pressure FAb is increased or not.

The respiratory drive is also changing during sleep. The most dramatic change is between non-rapid eye movement NREM and rapid eye movement REM sleep as the intercostal muscle activity drops to close to none during the REM period's skeletal muscle paralysis. During that time FTm is close to none while FAm remains constant.

Those changes directly affect the power loss calculations, so for the same PIt, the power loss will be different between periods where FTm, FTb, FAm or FAb change. For accurate us of RIP signals for evaluation of respiratory effort between patients or between periods within the night, it is preferable to use a modified power loss parameter that takes into account the forces FTm, FTb, FAm and FAb.

4. Measure of Multiple Time Variable Parameters Affecting Respiratory Effort

The forces FTm, FTb, FAm and FAb can be evaluated based on the RIP signals. A key parameter for such an evaluation are inhalation, exhalation, and respiration time, shape deviation between the thorax and abdomen signals along with the phase shift between the two.

During inhalation, all the forces FTp, FTm, FTb, FAp, FAm and FAb are present, but during exhalation, the muscle forces, FTm and FAm drop to zero, the PIt is reversed from higher negative to low positive values. The exhalation PIT values are relatively constant from breath to breath as the flow now opens the airway and the effect of the soft tissue causing the inhalation resistance is minimized. This means that the exhalation rate is dominated by the body pressure on the respiratory system only, which is driven by the FTb and FAb. The body forces are as mentioned above caused by the respiration thorax intercostal muscles stretching of the thorax and diaphragm pressing the inner organs of the abdomen. The energy used for this lifting is preserved, similar to compression of a spring in a mechanical system, so when the exhalation starts, the air is forced out by the energy stored in the stretched thorax and lifted abdomen. The exhalation time of Thorax vs. Abdomen is therefore directly relational to the amount of work that each system puts into the inhalation, that is, with exhalation time thorax=Tet and Aet for abdomen, the FTm/FAm is proportional to Tet/Aet. It is therefore important to use a measure of Tet and Aet in the calculation of respiratory effort to take into account the time variation of FTm, FAm ratio such as between non-rapid eye movement (NREM) and rapid eye movement (REM) sleep. Assuming the exhalation flow behaves as an exponent the body forces FTm and FAm are directly related to the exponent time constants for the thoracic exhalation $\tau T$ and the abdomen exhalation $\tau A$.

For a calibrated system, comparing the exhalation time at one point in the study, such as Tet1 to another Tet2 is of interest. As described above, the body force FTb and FAb changes with different body positions. If a patient is for example at time t1 in supine position and at t2 on left or right position, the FTb force could be significantly higher per liter inhaled at t2 compared with t1. The reason is that in supine position, the chest wall moves freely, while on the side, the bodyweight presses the chest wall that is touching the bed. For the same muscle effort, FTm at both times, the tidal volume inhaled by the chest is therefore lower on the side compared with the supine position. As the energy of inhalation going into thorax inhalation is conserved, the exhalation flowrate of the thorax will be the same for both t1 and t2. Comparing the exhalation time and volume from one point of the study to another provides an indicator that is proportional to the changes in FTb and FAb between those two points. This indicator can then be used to account for the changes in FTb and FAb when the respiratory effort is evaluated from the belts.

With an indicator on both the changes in FTm, FAm, FTb and FAb available, the inhalation time and the ratio of inhalation vs. exhalation time becomes of interest. For the same FTm, FAm, FTb and FAb, the ratio of inhalation vs. exhalation time is only variated by the FTp and FAp. The more negative the PIT becomes, the longer it takes to fill the lungs compared with exhaling. The inhalation time and exhalation time are therefore also important parameters for evaluating the actual respiratory effort.

As significant aspect of the present disclosure is that respiratory effort may be determined by adjusting components of a model of the respiratory system based on the thoracic effort signal (T), the abdomen effort signal (A), or the respiratory flow (F) or any combination of the thoracic effort signal (T), the abdomen effort signal (A), and the respiratory flow (F). In such a determination, the obtained thoracic effort signal (T) and the abdomen effort signal (A), with an obtained respiratory flow (F) are used, and one or more parameters in the model of the respiratory system so that the model can predict or provide a respiratory effort of the subject. The model dynamics set constraints on the solution space, and by fitting the model parameters using physical and temporal constraints the model can be used to predict or derive the respiratory effort of the subject. For example, fitting certain parameters during exhalation, fixing their values and fitting other parameters during inhalation the model can be fitted. Other factors such as setting the physical constraint that body parameters do not change rapidly between consecutive breaths, so a stable solution of the model can be found by identifying the model parameters which produce a good fit for multiple consecutive breaths. Similarly, a ratio may be derived of thoracic inhalation time versus thoracic exhalation time, a ratio of abdomen inhalation time versus abdomen exhalation time, and total inhalation time versus total exhalation time may be derived and used as parameters of the model.

Another parameter may be respiratory drive or changes in respiratory drive. Another parameter may be the thorax contribution to respiration or changes to thorax contribution. Another parameter may be abdomen and thoracic exhalation time constant, or changes in the exhalation time constant. Another parameter may be the intra thoracic pressure or changes in the intrathoracic pressure.

The abdomen and thoracic muscles force respiratory drive, and each element of the above model represents a part of the respiratory system. The fitted values of these elements represent some factor or parameter of the system. For example, the resistance represents the airway resistance. The muscle forces FTm and FAm represent the respiratory drive. And the relative partition of each element in respiration, the body forces FTb and FAb represent the force due to mass, elasticity, rigidity, and hydraulic pressure of the system, the areas At and Aa represent the coupling between the intrathoracic pressure and the thorax and abdomen, and the thoracic pressure PIT represents the intrathoracic pressure.

Further, the mass components of the subject's body may be parameters. If mass is not included in the model may cause the model to oscillate and have infinitely short reaction times. Accordingly, various mass components, such as thoracic or abdomen masses can be helpful parameters.

Further, parameter surrogate to respiratory effort or intrathoracic pressure can be measured using the RIP belts and possibly flow. It is further significant that the parameters of the model may be fit using the RIP measurements combined with a directly measured or an alternatively derived respiratory flow to determine the respiratory effort.

Other parameters that are directly affected by the respiratory effort level are the divergence between the two belt signals, the phase between the two belt signals, changes in respiratory rate, and of cause the power loss of the sum.

5. Patient to Patient Comparison

It is clear that patients are different in general and patient to patient comparison must account for that difference when comparing the respiratory effort calculations. For example children have softer rib cages compared with adults, causing higher power loss for a given PIt compared with the adult. A general method to account for such differences is to use normalization towards a normal breath of a particular patient. During sleep studies, a patient will have a number of breaths that have low respiratory effort, such as before the study start and during the night after position changes etc. Those breaths can be easily identified as they will have relatively similar inhalation and exhalation time. The higher the power loss of the sum is measured compared to the inhalation/exhalation time ratio, the softer is the rib-cage. Selecting breaths and applying those parameters can therefore be used to create an additional weight on the measured power loss to make it comparable from one patient to the other.

6. Multi-Parameter Modeling of Respiratory Effort

From the above description, we have the following.

A method is provided for evaluating the ratio of the signal loss $S_l$ in the calibrated sum by first applying the methods of 1, 2, or 3 to evaluate $k_A$, then using the $k_A$ to create a weighted sum between signals based on T and A and then calculating the ratio between the amplitude, power or any transformation f of this sum towards the sum of the amplitudes, power or any other transformation f of each of the signals derived from the T and A. E.g.

$$\frac{f(T+k_A A)}{f(T)+f(k_A A)} \text{ or } \frac{f(T'+k_A A')}{f(T')+f(k_A A')} \text{ or } \frac{f(T'+k_A A')}{f(T)+f(k_A A)}$$

It is now clear that this formula does indeed describe respiratory effort accurately for a given patient, body position and sleep stage. It does however need to take the parameters mentioned above into account to maximize the comparability between patients, body positions and sleep stages. This can be done using linear or non-linear multi-parameter modeling. The method measures all of the above parameters and feeds them into a function that transforms them into an output value indicating the respiratory effort. Typically this would be done by "training" the linear or non-linear model on the input parameters to best describe the known output values for respiratory effort. The known output values would be derived from invasive measurements, such as direct or indirect measure of intra thoracic pressure PIT and/or diaphragm and intercostal muscle EMG.

When a model has been trained, the model parameters can be used to identify all forces, pressures and resistances depicted in FIG. 11. Furthermore, the model can be used to identify other parameters such as the thoracic and abdomen exhalation time constants τT and τA, respectively. The respiratory drive or intended volume, can be identified directly from the model or by using the derived parameters and setting the airway resistance Rr to a low value. The relative contribution of the thorax and abdomen to breathing can be identified.

For RIP based respiratory parameters R={r1, r2, r3 ... rn} and the effort values E={e1, e2, e3 ... em} the general formulas to describe such a relationship would be E=B×R for a linear transformation while it would go E=F(R) for non-linear transformation.

There are multiple methods to find the optimal formulas describing this relationship. For example, for linear transformation, the use of Kalman filtering to describe the transformation matrix B is a standard method in engineering, while for seeking a non-linear relationship for describing the transformation F(R) is commonly done by using artificial neural networks with parameters optimized to with the R to E relationship.

According to the present disclosure, the following embodiments and combinations of embodiments are provided: In a first embodiment, embodiment 1: A method for calibration of respiratory effort signals is provided where:

at least Thorax effort signal T and Abdomen effort signal A are measured, where T and A signals are composed of the sum of at least two different signal components each, where at least one signal component ($V_{ST}$) in T and one signal, component ($V_{SA}$) in A both have the same shape as the actual respiratory volume, that is they are positively proportional to the actual respiratory volume, where at least one component $P_T$ in T is negatively proportional to a component $P_A$ in A, where the weighted sum of the T and A signals is used to derive a Volume proportional signal $V_S$, where the ratio of the weights for A towards T is $k_A$, and where $k_A$ is selected by seeking a value of $k_A$ that minimizes the residues of the $P_T$ and $P_A$ components in the resulting sum $V_S$ In embodiment 2, further to the embodiment 1 above or any of the embodiments below, instead of processing the respiratory effort signals T and A, the first derivative of T (T') and A (A') are used instead of the T and A to minimize the residues of the $P_T$ and $P_A$ resulting in a Respiratory Flow proportional signal $F_S$.

In embodiment 3, further to any of the embodiments above or below, any level of integration or derivative of T and A are used.

In embodiment 4, further to any of the embodiments above or below, the proportional power of the lower frequencies are maximized compared with the higher frequencies over a period of time.

In embodiment 5, further to any of the embodiments above or below, the amplitude loss and/or power loss of the resulting signal is maximized compared with the sum of the amplitudes and/or power of T and A over a period of time.

In embodiment 6, further to any of the embodiments above or below, by first applying the methods described in embodiments 4 and/or 5 to derive the ratio for shorter timespans within the longer period, the performance of the methods is weighted for each timespan before choosing a $k_A$ for the longer period based on selecting the methods providing the most optimal result.

In embodiment 7, further to any of the embodiments above or below, the method further includes weighting in the $k_A$ values of the other periods within the set to maximize the continuity and level of determination over the whole set.

In embodiment 8, further to any of the embodiments above or below, the method further includes deriving the residual signal $P_T$, or any derivative or integer of $P_T$ from T and A signals by first applying the methods described in 1, 2, or 3, and then use the resulting signal $V_S$ to seek for the thorax and abdomen contribution ratio that results in minimizing of the amplitude and/or power of $P_T$.

In embodiment 9, a method is provided for evaluating flow resistance from the ratio of $P_T$ defined in equation (9) with the first derivative of $V_S$.

In embodiment 10, a method is provided for evaluating respiration energy by integrating the multiply of $P_T$ defined in equation (9) with the first derivative of $V_S$ In embodiment 11, a method is provided for evaluating the ratio of the signal loss $S_l$ in the calibrated sum by first applying the methods of embodiments 1, 2, or 3, above, to evaluate $k_A$, then using the $k_A$ to create a weighted sum between signals based on T and A and then calculating the ratio between the amplitude, power or any transformation f of this sum towards the sum of the amplitudes, power or any other transformation f of each of the signals derived from the T and A:

$$\frac{f(T + k_A A)}{f(T) + f(k_A A)} \text{ or } \frac{f(T' + k_A A')}{f(T') + f(k_A A')}.$$

In embodiment 12, a method is provided for further stabilizing the amplitude of the signals derived by embodiments 1, 2, or 3, by first calculating the $V_S$, then based on the $V_S$, calculate an integrated volume ($V_I$) by summing the tidal volumes from the $V_S$ over a period of time, and for the same period of time monitor the average heart rate (HR) signal. Then adjust the absolute amplitude of $V_S$, by using the approximation that the ratio of $V_I$ towards HR is close to constant for all periods.

In embodiment 13, the method described in embodiment 12 is applied by using HR signal derived by isolating the cardiac component from the T or A signals.

In embodiment 14, the method described in embodiment 12 is applied by using HR signal derived from pulse Oximeter or ECG electrodes.

Additionally, according to the present disclosure, the following embodiments, the following embodiments and combinations of embodiments are provided:

In embodiment 15, a method is provided for evaluating the ratio of the signal loss $S_l$ in the calibrated sum by first applying the methods of embodiments 1, 2, or 3, above, to evaluate $k_A$, then using the $k_A$ to create a weighted sum between signals based on T and A and then calculating the ratio between the amplitude, power or any transformation f of this sum towards the sum of the amplitudes, power or any other transformation f of each of the signals derived from the T and A:

$$\frac{f(T' + k_A A')}{f(T) + f(k_A A)}.$$

In embodiment 16, further to any of the embodiments above or below, a model is used based on plurality of parameters derived from RIP signals to predict respiratory effort in a patient.

In embodiment 17, further to any of the embodiments above or below, any or all of the following parameters are used to build a respiratory effort model, measured from the RIP signals, Power Loss, Inhalation time, Exhalation time, Inhalation volume, Exhalation volume, Exhalation flow, Inhalation flow, Respiratory Rate, Total volume over certain time, such as minute volume, shape divergence between belts, phase between belts and/or time shift between belts.

In embodiment 18, further to any of the embodiments above or below, breaths are selected for patient normalization and using a subset or all of the above mentioned parameters to create a respiratory effort scale comparable between patients.

In embodiment 19, further to any of the embodiments above or below, general patient information is used, such age, weight, height or other body measures and/or conditions to further improve the respiratory effort measure.

In embodiment 20, further to any of the embodiments above or below, time periods of constant calibration are identified by looking for sudden changes in any or all of the above mentioned parameters.

Each of the methods described herein, or any combination of the above-described methods may be implemented by a respiratory effort measuring system that includes a first sensor device configured to obtain a thorax effort signal (T) and a second sensor device configured to obtain an abdomen effort signal (A). As above, the thorax effort signal (T) being an indicator of a thoracic component of the respiratory effort. And as above, the abdomen effort signal (A) being an indicator of an abdominal component of the respiratory effort. The system may include a memory storage configured to store data of each of the thorax effort signal (T) and the abdomen effort signal (A). The system may further include a processor, such as one of more hardware processor devices. For example, the processor may be one or more processors of a computer or a terminal device. The processor of the system is configured to receive the thorax effort signal (T) and the abdomen effort signal (A).

Further, the processor is configured to obtain a respiratory flow (F) of the subject. The respiratory flow (F) of the subject may be measured directly by a sensor or device of the system, such as respiratory flow sensor included in the respiratory effort measuring system. For example, the respiratory effort measuring system may include a cannula flow sensor that directly measures the respiratory flow (F) of the subject. For example, the system may include one or more pneumo flow sensors. Or alternatively, the respiratory flow (F) may be determined or derived based on other obtained signals, such as effort bands or belts placed on the subject. For example, the respiratory flow (F) may be determined from RIP signals, as described herein. For example, a respiratory flow (F) may be obtained by deriving the respiratory flow (F) from a calibrated RIP signal sum. Or alternatively, a respiratory flow (F) may be obtained by deriving the respiratory flow (F) from non-calibrated RIP signals. Such derivation of the respiratory flow (F) may further be performed by the processor of the system.

Further, obtaining either a thoracic effort signal (T) and/or an abdomen effort signal (A) could be performed by directly measuring the thoracic effort signal (T) and/or the abdomen effort signal (A), or the thoracic effort signal (T) and/or the abdomen effort signal (A) may be obtained from previously recorded signals that have been received, for example, but RIP sensor belts, effort bands or other sensors placed on a subject for a period of time and then data from the signals are stored in a data storage device, such as a hardware storage device, from which the thoracic effort signal (T) and/or the abdomen effort signal (A), or in other words, the data of the thoracic effort signal (T) and/or the abdomen effort signal (A) are obtained.

In another embodiment, a hardware storage device is provided. Such a storage device may be any hardware device that is used for storing, porting and extracting data files and objects, which can hold and store information both temporarily and permanently. The storage device may be internal or may be external to a computer, server or any similar computing device. The hardware storage device has stored thereon computer executable instructions which, when executed by one or more processors, implement a method of measuring respiratory effort of a subject. The method includes obtaining a thoracic effort signal (T), obtaining an abdomen effort signal (A), and obtaining a respiratory flow (F). The thoracic effort signal (T) is an indicator of a thoracic component of the respiratory effort. The abdomen effort signal (A) is an indicator of an abdominal component of the respiratory effort. The method further includes determining the respiratory effort by adjusting the components of a model of the respiratory system based on the thoracic effort signal (T), the abdomen effort signal (A), or the respiratory flow (F), or any combination of the thoracic effort signal (T), the abdomen effort signal (A), and the respiratory flow (F).

Certain terms are used throughout the description and claims to refer to particular methods, features, or components. As those having ordinary skill in the art will appreciate, different persons may refer to the same methods, features, or components by different names. This disclosure does not intend to distinguish between methods, features, or components that differ in name but not function. The figures are not necessarily to scale. Certain features and components herein may be shown in exaggerated scale or in somewhat schematic form and some details of conventional elements may not be shown or described in interest of clarity and conciseness.

Although various example embodiments have been described in detail herein, those skilled in the art will readily appreciate in view of the present disclosure that many modifications are possible in the example embodiments without materially departing from the concepts of present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scopes of the disclosure and the appended claims. Each addition, deletion, and modification to the embodiments that falls within the meaning and scope of the claims is to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges may appear in one or more claims below. Any numerical value is "about" or "approximately" the indicated value, and takes into account experimental error and variations that would be expected by a person having ordinary skill in the art.

What is claimed:

1. A method of determining a value of one or more parameters of a respiratory effort of a subject, the method comprising:
obtaining a thoracic signal (T), the thoracic signal (T) being an indicator of a thoracic component of the respiratory effort, the thoracic signal (T) being a thoracic respiratory inductive plethysmograph (RIP) signal;
obtaining an abdomen signal (A), the abdomen signal (A) being an indicator of an abdominal component of the respiratory effort, the abdomen signal (A) being an abdomen respiratory inductive plethysmograph (RIP) signal; and
determining, without directly measuring, the value of the one or more parameters of the respiratory effort by using constraints and/or relationships of components of a model of a respiratory system of the subject, and fitting the components of the model of the respiratory system of the subject with data from the obtained thoracic signal (T) and data from the obtained abdomen signal (A),
wherein each of the determined one or more parameters of the respiratory effort is different than each of
the thoracic component of the respiratory effort,
the abdominal component of the respiratory effort,
a weighted thoracic component of the respiratory effort,
a weighted abdominal component of the respiratory effort,
a paradox component of the respiratory effort, and
a respiratory movement; and
wherein the one or more parameters include one or more of:
an airway resistance Rr of the subject;
an intercostal muscle drive force FTm;
a diaphragm drive force FAm;
an intrathoracic pressure PIt;
respiratory drive;
a thoracic negative pressure force FTp; and
an abdomen negative pressure force FAp.

2. The method according to claim 1, wherein the one or more parameters includes at least a thoracic negative pressure force FTp.

3. The method according to claim 2, wherein the thoracic negative pressure force FTp is based on an additional force caused by an intrathoracic pressure PIt across a thoracic area (At), such that FTp=PIt*At.

4. The method according to claim 1, wherein the one or more parameters includes at least an abdomen negative pressure force FAp.

5. The method according to claim 4, wherein the abdomen negative pressure force FAp is based on an additional force caused by an intrathoracic pressure PIt across an Abdomen area (Aa), such that FAp=PIt*Aa.

6. The method according to claim 5, wherein
low airway resistance Rr of the subject results in low thoracic negative pressure force FTp and/or low abdomen negative pressure force FAp, or
high airway resistance Rr of the subject results in high thoracic negative pressure force FTp and/or high abdomen negative pressure force FAp.

7. The method according to claim 5, wherein low airway resistance Rr indicates that an upper airway resistance is low.

8. The method according to claim 1, wherein the thoracic signal (T) and abdomen signal (A) are obtained by a Respiratory Inductive Plethysmograph (RIP) system, including a first stretchable belt including a first conductor formed therein, the first stretchable belt being arranged at a thoracic region of the subject, and a second stretchable belt including a second conductor formed therein, the second stretchable belt being arranged at an abdomen of the subject, and a processing unit configured to obtain the thoracic signal (T) as a first inductive signal from the first conductor and the processing unit is configured to obtain the abdomen signal (A) as a second inductive signal from the second conductor.

9. The method according to claim 1, wherein any one or more of intercostal muscle drive force FTm, a thorax counterforce FTb, a diaphragm drive force FAm, an abdomen counterforce FAb are determined based on a Respiratory Inductive Plethysmograph (RIP) system, including a first stretchable belt including a first conductor formed therein, the first stretchable belt being arranged at a thoracic region of the subject, and a second stretchable belt including a second conductor formed therein, the second stretchable belt being arranged at an abdomen of the subject, and a processing unit configured to obtain the thoracic signal (T) as a first inductive signal from the first conductor and the processing unit is configured to obtain the abdomen signal (A) as a second inductive signal from the second conductor.

10. The method according to claim 1, wherein any one or more of intercostal muscle drive force FTm, a thorax counterforce FTb, a diaphragm drive force FAm, an abdomen counterforce FAb are determined based on an evaluation of one or more inhalations.

11. The method according to claim 1, wherein any one or more of intercostal muscle drive force FTm, a thorax counterforce FTb, a diaphragm drive force FAm, an abdomen counterforce FAb are determined based on an evaluation of one or more exhalations.

12. The method according to claim 1, wherein any one or more of intercostal muscle drive force FTm, a thorax counterforce FTb, a diaphragm drive force FAm, an abdomen counterforce FAb are determined based on an evaluation of one or more respiration times.

13. The method according to claim 1, wherein any one or more of intercostal muscle drive force FTm, a thorax counterforce FTb, a diaphragm drive force FAm, an abdomen counterforce FAb are determined based on an evaluation of one or more shape deviations between the thorax signal (T) and the abdomen signal (A).

14. The method according to claim 1, wherein any one or more of intercostal muscle drive force FTm, a thorax counterforce FTb, a diaphragm drive force FAm, an abdomen counterforce FAb are determined based on an evaluation of one or more phase shifts between the thorax signal (T) and the abdomen signal (A).

15. The method according to claim 1, wherein the determining of the value of the one or more parameters of the respiratory effort is further based on a ratio of inhalation time versus exhalation time, and
wherein a determination of intrathoracic pressure is determined based on a ratio of inhalation time versus exhalation time, where it is assumed that PIt becomes more negative the longer it takes to fill a respiratory capacity compared with an exhalation time.

16. The method according to claim 1, wherein determining, without directly measuring the value of the one or more parameters of the respiratory effort includes
determining, without directly measuring, a weighted sum (S) of the thoracic signal (T) and the abdomen signal (A) that correctly represents the respiratory volume by the relative contribution of the thoracic signal (T) and the abdomen signal (A) to two or more harmonics of the weighted sum (S).

17. The method according to claim 1, wherein the one or more parameters include an airway resistance Rr of the subject.

18. The method according to claim 1, wherein the one or more parameters include an intercostal muscle drive force FTm.

19. The method according to claim 1, wherein the one or more parameters include a diaphragm drive force FAm.

20. The method according to claim 1, wherein the one or more parameters include an intrathoracic pressure Plt.

21. The method according to claim 1, wherein the one or more parameters include respiratory drive.

22. A system for determining a value of one or more parameters of a respiratory effort of a subject, the system comprising:
a first sensor device configured to obtain a thorax signal (T), the thorax signal (T) being an indicator of a thoracic component of the respiratory effort, the thoracic signal (T) being a thoracic respiratory inductive plethysmograph (RIP) signal;
a second sensor device configured to obtain an abdomen signal (A), the abdomen signal (A) being an indicator of an abdominal component of the respiratory effort, the abdomen signal (A) being an abdomen respiratory inductive plethysmograph (RIP) signal;
a processor configured to receive the thorax signal (T) and the abdomen signal (A);
wherein the processor further is configured to
receive the thorax signal (T),
receive an abdomen signal (A), and
determine, without directly measuring, the value of the one or more parameters of the respiratory effort by
using constraints and/or relationships of components of a model of a respiratory system of the subject, and
fitting the components of the model of the respiratory system of the subject with data from the obtained thoracic signal (T) and data from the obtained abdomen signal (A),
wherein each of the determined one or more parameters of the respiratory effort is different than each of
the thoracic component of the respiratory effort,
the abdominal component of the respiratory effort,
a weighted thoracic component of the respiratory effort,
a weighted abdominal component of the respiratory effort,
a paradox component of the respiratory effort, and
a respiratory movement; and
wherein the one or more parameters include one or more of:
an airway resistance Rr of the subject;
an intercostal muscle drive force FTm;
a diaphragm drive force FAm;
an intrathoracic pressure Plt;
respiratory drive;
a thoracic negative pressure force FTp; and
an abdomen negative pressure force FAp.

23. A hardware storage device having stored thereon computer executable instructions which, when executed by one or more processors, implement a method of determining a value of one or more parameters of a respiratory effort of a subject, the method comprising:
obtaining a thoracic signal (T), the thoracic signal (T) being an indicator of a thoracic component of the respiratory effort, the thoracic signal (T) being a thoracic respiratory inductive plethysmograph (RIP) signal;
obtaining an abdomen signal (A), the abdomen signal (A) being an indicator of an abdominal component of the respiratory effort, the abdomen signal (A) being an abdomen respiratory inductive plethysmograph (RIP) signal; and
determining, without directly measuring, the value of the one or more parameters of the respiratory effort by
using constraints and/or relationships of components of a model of a respiratory system of the subject, and
fitting the components of the model of the respiratory system of the subject with data from the obtained thoracic signal (T) and data from the obtained abdomen signal (A),
wherein each of the determined one or more parameters of the respiratory effort is different than each of
the thoracic component of the respiratory effort,
the abdominal component of the respiratory effort,
a weighted thoracic component of the respiratory effort,
a weighted abdominal component of the respiratory effort,
a paradox component of the respiratory effort, and
a respiratory movement; and
wherein the one or more parameters include one or more of:
an airway resistance Rr of the subject;
an intercostal muscle drive force FTm;
a diaphragm drive force FAm;
an intrathoracic pressure Plt;
respiratory drive;
a thoracic negative pressure force FTp; and
an abdomen negative pressure force FAp.

* * * * *